(12) United States Patent
Yovell

(10) Patent No.: US 10,813,925 B2
(45) Date of Patent: Oct. 27, 2020

(54) BUPRENORPHINE FOR THE TREATMENT OF ACUTE SUICIDALITY

(71) Applicant: Carmel-Haifa University Economic Corporation Ltd., Haifa (IL)

(72) Inventor: Yoram Yovell, Mevaseret Zion (IL)

(73) Assignee: Carmel—Haifa University Economic Corporation Ltd., Haifa (IL)

( * ) Notice: Subject to any disclaimer, the term of this patent is extended or adjusted under 35 U.S.C. 154(b) by 467 days.

(21) Appl. No.: 14/345,695

(22) PCT Filed: Sep. 19, 2012

(86) PCT No.: PCT/IB2012/054971
§ 371 (c)(1),
(2) Date: Mar. 19, 2014

(87) PCT Pub. No.: WO2013/042054
PCT Pub. Date: Mar. 28, 2013

(65) Prior Publication Data
US 2014/0235663 A1 Aug. 21, 2014

Related U.S. Application Data

(60) Provisional application No. 61/536,081, filed on Sep. 19, 2011.

(51) Int. Cl.
*A61K 31/485* (2006.01)

(52) U.S. Cl.
CPC .................. *A61K 31/485* (2013.01)

(58) Field of Classification Search
None
See application file for complete search history.

(56) References Cited

U.S. PATENT DOCUMENTS

| | | |
|---|---|---|
| 6,528,518 B2 | 3/2003 | Carlezon, Jr. |
| 8,173,695 B2 | 5/2012 | Diaz Buezo et al. |
| 2004/0181475 A1 | 9/2004 | Haroon |
| 2004/0242974 A1 | 12/2004 | Glover |
| 2006/0216340 A1 | 9/2006 | Reder et al. |
| 2010/0048535 A1 | 2/2010 | Slater et al. |
| 2011/0039926 A1 | 2/2011 | Mansuy |

FOREIGN PATENT DOCUMENTS

| WO | WO 03/079945 | 10/2003 |
|---|---|---|
| WO | WO 2013/042054 | 3/2013 |

OTHER PUBLICATIONS

Yovel et al.(2) ClinicalTrials.gov—NCT00863291 on Mar. 16, 2009. Phase 3 Study of the Effects of Buprenophine as Add-on Treatment to Antidepressants in Treating Acutely Suicidal Depressed Inpatients).*

Sittl et al.. "Analgesic efficacy and tolerability of transdermal buprenorphine in patients with inadequately controlled chronic pain related to cancer and other disorders: a multicenter, randomized, double-blind, placebo-controlled trial." Clinical therapeutics 25.1 (2003): 150-168.*
Supplementary European Search Report and the European Search Opinion dated Feb. 13, 2015 From the European Patent Office Re. Application No. 12833132.9.
Maremmani et al. "Do Methadone and Buprenorphine Have the Same Impact on Psychopathological Symptoms of Heroin Addicts?", Annals of General Psychiatry, XP021101199, 10(17): 1-8, May 15, 2011. Conclusions.
Maremmani et al. "Substance Use and Quality of Life Over 12 Months Among Buprenorphine Maintenance-Treated and Methadone Maintenance-Treated Heroin-Addicted Patients", Journal of Substance Abuse Treatment, XP022121481, 33(1): 91-98, Jul. 2007. Para [03.2].
International Search Report and the Written Opinion dated Feb. 1, 2013 From the International Searching Authority Re. Application No. PCT/IB2012/054971.
Abarbanel Mental Health Center "A Double-Blind Study of Buprenorphine Treatment of Acute Suicidality", Abarbanel Mental Health Center, Israel, ClinicalTrials.gov, Mar. 16, 2009.
Bar et al. "A Double Blind Study of Buprenorphine Treatment of Acute Suicidality", Montreal—Abstracts Research Day, 2011.
Barbui et al. "Selective Serotonin Reuptake Inhibitors and Risk of Suicide: A Systematic Review of Observational Studies", CMAJ, Canadian Medical Association Journal, 180(3): 291-297, Feb. 3, 2009.
Beasley Jr. et al. "Fluoxetine and Suicide: A Meta-Analysis of Controlled Trials of Treatment for Depression", BMJ, 303: 685-692, 1991.
Bertolote et al. "A Global Perspective in the Epidemiology of Suicide", Suicidologi, 7(2): 6-8, 2002.
Bodkin et al. "Buprenorphine Treatment of Refractory Depression", Journal of Clinical Psychopharmacology, 15: 49-57, 1995.
Callaway "Buprenorphine for Depression: The Un-Adoptable Orphan", Biological Psychiatry, 39: 989-990, 1996.
DeWall et al. "Acetaminophen Reduces Social Pain: Behavioral and Neural Evidence", Psychological Science, 21(7): 931-937, 2010.
Drummond "Spray of Hope. Military Developing Anti-Suicide Nasal Spray as Deaths Hit Record Numbers", The Daily, Aug. 17, 2012.

(Continued)

*Primary Examiner* — Layla Soroush

(57) ABSTRACT

Methods and compositions for treating acute suicidality by administration of buprenorphine are disclosed herein. An exemplary method is effected by administering to a subject determined as having acute suicidality a first therapeutically effective amount of buprenorphine, or a pharmaceutically acceptable salt thereof, whereby the administration is ceased once the subject is no longer determined as having acute suicidality. The first therapeutically effective amount is less than 0.2 mg per day. A higher therapeutically effective amount may optionally be administered if the subject is determined as not fully responsive to the first therapeutically effective amount. Unit dosage forms of buprenorphine, comprising less than 0.2 mg (e.g., 0.1 mg) buprenorphine are also disclosed.

12 Claims, 10 Drawing Sheets

(56) References Cited

OTHER PUBLICATIONS

Ehrich et al. "Early Clinical Development of the Opioid Modulator ALKS 5461 in the Treatment of the Depression and Addiction", NCDEU, New Research Approaches for Mental Health Interventions, Poster Session 1, May 30, 2012.

Eisenberger et al. "Why Rejection Hurts: A Common Neural Alarm System for Physical and Social Pain", Trends in Cognitive Sciences, 8(7): 294-300, Jul. 2004.

Emrich et al. "Possible Antidepressive Effects of Opioids: Action of Buprenorphine", Annals of the New York Academy of Sciences, 398: 108-112, 1982.

Gunnell et al. "Antidepressants and Suicide: What Is the Balance of Benefit and Harm", British Medical Journal, BMJ, 329: 34-38, Jul. 3, 2004.

Hammad et al. "Suicidality in Pedriatric Patients Treated With Antidepressants Drugs", Archives of General Psychiatry, 63(3): 332-339, Mar. 2006.

Jick et al. "Antidepressants and the Risk of Suicidal Behaviors", Journal of the American Medical Association, JAMA, 292(3): 338-343, Jul. 21, 2004.

Juurlink et al. "The Risk of Suicide With Selective Serotonin Reuptake Inhibitors in the Elderly", American Journal of Psychiatry, 163(5): 813-821, May 2006.

Keilp et al. "Suicidal Ideation and the Subjective Aspects of Depression", Journal of Affective Disorders, 140: 75-81, 2012.

Khan et al. "Suicide Rates in Clinical Trials of SSRIs, Other Antidepressants, and Placebo: Analysis of FDA Reports", American Journal of Psychiatry, 160(4): 790-792, Apr. 2003.

Kosten et al. "Depressive Symptoms During Buprenorphine Treatment of Opioid Abusers", Journal of Substance Abuse Treatment, 7: 51-54, 1990.

Kross et al. "Social Rejection Shares Somatosensory Representations With Physical Pain", Proc. Natl. Acad. Sci. USA, PNAS, 108(15): 6270-6275, Apr. 12, 2011.

Lönnqvist "Major Psychiatric Disorders in Suicide and Suicide Attempters", Oxford Textbook of Suicidology and Suicide Prevention, Part 6: Psychiatric and Somatic Determinants of Suicide, Chap.38: 275-286, 2009.

Maremmani et al. "Effectiveness of Buprenorphine in Double Diagnosed Patients. Buprenorphine as Psychothropic Drug", Heroin Addiction & Related Clinical Problems, 8(1): 31-48, 2006.

Mongan et al. "Buprenorphine Responders", Biological Psychiatry, 28: 1078-1080, 1990.

Orbach et al. "Mental Pain and Its Relationship to Suicidality and Life Meaning", Suicide and Life Threatening Behavior, 33(3): 231-241, Fall 2003.

Resnick et al. "Buprenorphine: Pilot Trials in Borderline Patients and Opiate Dependence—Treatment of a Common Disorder?", Problems of Drug Dependence 1987, Proceedings of the 49th Annual Scientific Meeting, The Committee on Problems of Drug Dependence, NIDA Research Monograph, 81: 298, 1988.

Sporer "Buprenorphine: A Primer for Emergency Physicians", Annals of Emergency Medicine, 43(5): 580-584, May 2004.

Stanley et al. "The Interpersonal Dimension of Borderline Personality Disorder: Toward a Neuropeptide Model", American Journal of Psychiatry, 167(1): 24-39, Jan. 2010.

Yovell et al. "A Double-Blind Study of Buprenorphine Treatment of Acute Suicidality", DrugLib.com, Jan. 13, 2010.

Bershad et al. "Opioid Partial Agonist Buprenorphine Dampens Responses to Psychosocial Stress in Humans", Psychoneuroendocrinology, 52: 281-288, Published Online Dec. 9, 2014.

Karp et al. "Safety, Tolerability, and Clinical Effect of Low-Dose Buprenorphine for Treatment-Resistant Depression in Mid-Life and Older Adults", Journal of Clinical Psychiatry, 75(8): e785-e793, Aug. 2014.

Norelli et al. "Buprenorphine in the Treatment of Non-Suicidal Self-Injury: A Case Series and Discussion of the Literature", International Journal of Adolescent Medicine and Health, 25(3): 323-330, 2013.

Schatzberg "Opioids in Psychiatric Disorders: Back to the Future?", The American Journal of Psychiatry, p. 1-2, AJP in Advance Dec. 18, 2015.

Yovell et al. "Ultra-Low-Dose Buprenorphine as a Time-Limited Treatment for Severe Suicidal Ideation: A Randomized Controlled Trial", The American Journal of Psychiatry, Data Supplement, p. 1-6, 2015.

Yovell et al. "Ultra-Low-Dose Buprenorphine as a Time-Limited Treatment for Severe Suicidal Ideation: A Randomized Controlled Trial", The American Journal of Psychiatry, p. 1-8, Ahead of Print 2015 & Data Supplement, p. 1-6, 2015.

Communication Pursuant to Article 94(3) EPC dated Nov. 24, 2016 From the European Patent Office Re. Application No. 12833132.9. (3 Pages).

Communication Pursuant to Article 94(3) EPC dated Sep. 11, 2017 From the European Patent Office Re. Application No. 12833132.9. (3 Pages).

Office Action dated Apr. 16, 2018 From the Israel Patent Office Re. Application No. 231593 and Its Translation Into English. (7 Pages).

* cited by examiner

BUPRENORPHINE FOR THE TREATMENT OF ACUTE SUICIDALITY

FIELD AND BACKGROUND OF THE INVENTION

The present invention, in some embodiments thereof, relates to therapy and, more particularly, but not exclusively, to methods, and compositions for the treatment of acute suicidality.

Suicide is a major cause of death worldwide, and more than a million people die by suicide every year [Bertolote et al., *Suicidology* 2:6-8 (2002)]. 60% of suicides are performed by people suffering from depression or other mood disorders. However, depression explains only a portion of suicides, which has led to the hypothesis that the primary motivation for suicide is psychache—intense emotional and psychological pain that eventually becomes intolerable—which may or may not be associated with depression [Shneidman, *Suicide as psychache: A clinical approach to self-destructive behavior*. Northvale, N.J.: Aronson. (1993)].

As of now, there are no effective pharmacological treatments for acute suicidality. Many suicidal patients receive antidepressant medications. However, typical antidepressant medications, such as selective serotonin reuptake inhibitors (SSRI), require several weeks in order to exhibit a significant therapeutic effect. Despite their established antidepressant effect, it is doubtful whether antidepressant medications exhibit a direct anti-suicidal effect [Gunnell & Ashby, *BMJ*, 329:34-38 (2004); Beasley et al., *BMJ*, 303, 685-92 (1991); Kahn et al., *J Clin Psychiatry*, 160:790-792 (2003)], particularly during the first few months of treatment, and some recent evidence suggests that antidepressant medications may lead to an actual increase in the incidence of suicide, e.g., during the first few weeks of antidepressant therapy [Hammad et al., *Arch Gen Psychiatry*, 63:332-339 (2006); Jick et al., *JAMA* 292:338-343 (2004); Juurlink et al., *Am J Psychiat*, 163:813-821 (2006)].

Several lines of evidence have recently suggested that suicidality, while being one of the symptoms of depression, is at least partially independent of depression, and may respond differently to treatment [reviewed by Lönnqvist, in Wasserman & Wasserman, *Suicidology and suicide prevention*. New York, N.Y.: Oxford (2009), 275-286]. Depression severity is only modestly associated with the presence and severity of suicidal ideation, and this association is decreased when specific items assessing suicidal thinking (as opposed to somatic and vegetative symptoms) are removed from the depression scales. It has been suggested that this may explain why suicide risk remains high during treatment with antidepressants, even though somatic and vegetative symptoms improve [Keilp et al., *J Affecive Disorders*, 140:75-81 (2012)].

Unbearable mental pain has been reported to be a strong and independent predictor of suicidality [Orbach et al., *Suicide Life Threat Behav*, 33:231-241 (2003)]. Experiencing physical pain and feeling the mental pain of social loss and rejection were found to involve the same brain regions, neural pathways, and neurotransmitters, especially endorphins (endogenous opioids) [Eisenberger & Lieberman, *Trends Cogn Sci* 8:294-300 (2004); Kross et al., *Proc Natl Acad Sci USA* 108:6270-6275 (2011)].

Acetaminophen, a common pain relief medication, was reported to reduce the pain of social rejection [DeWall et al., *Psychological Science* 21:931 (2010)].

The U.S. Army has begun investigation of a nasal spray for administering TRH (thyrotropin-releasing hormone), for use as an anti-suicide treatment ["SPRAY OF HOPE, Military developing anti-suicide nasal spray as deaths hit record numbers", *The Daily*, Aug. 17, 2012].

Opioids, which are the most potent pharmacological agents for the treatment of physical pain, were used from the 1850's to the 1950's to treat depression, but because of their abuse potential, they were replaced by electroconvulsive therapy, tricyclic antidepressants and monoamine oxidase inhibitors once these treatments became available.

Buprenorphine is a mixed opioid agonist-antagonist, derived from thebaine. Buprenorphine exhibits a strong affinity towards µ-opioid receptors with a long-lasting effect, acting as a highly potent agonist at low concentrations (e.g., 25-40 times as potent an analgesic as morphine). However, at high concentrations the effect of buprenorphine is antagonistic rather than agonistic. This ceiling effect of buprenorphine diminishes its abuse potential, and results in low toxicity and mild withdrawal symptoms [Sporer, *Ann Emerg Med*, 43:580-584 (2004)]. Because of these characteristics, buprenorphine is used in narcotic detoxification and in maintenance programs for people with opioid dependence, typically at doses of at least 8 mg per day, and in lower doses, as an analgesic.

Bodkin et al. [*J Clin Psychopharmacol* 15:49-57 (1995)] and Emrich et al., [*Ann NY Acad Sci*, 398:108-112 (1982)] describe the use of buprenorphine for treating refractory depression. Buprenorphine was reported to reduce depressive symptoms in psychiatric patients diagnosed with depression with a high co-morbidity to other disorders [Morgan & Callaway, *Biol Psychiatry*, 28:1078-1080 (1990)], in opioid abusers [Kosten et al., *J Subst Abuse Treat*, 7:51-54 1990)], and in patients with borderline personality disorder [Resnick & Falk, In Harris, L. S. (Ed.), *Problems of drug dependence*. Washington, D.C.: National Institute on Drug Abuse Research (1987)].

Callaway [*Biol Psychiatry* 39:989-990 (1996)] describes buprenorphine as being effective for treating depression, but unlikely to be marketed for use as an antidepressant in the foreseeable future, due to a strong anti-narcotic bias among the professional and lay communities in the U.S., and among the U.S. regulatory and research authorities.

U.S. Patent Application No. 2004/0181475 describes a method using transdermal delivery of buprenorphine, with incremental escalation of buprenorphine dose, for treating depression At the 52nd Annual New Clinical Drug Evaluation Unit (NCDEU) meeting (sponsored by the National Institute of Mental Health), Alkermes reported positive results over a 7-day treatment period from a phase I/II study of ALKS 5461, a combination of buprenorphine and an opioid modulator (ALKS 33), for major depressive disorder (MDD) in patients who have an inadequate response to standard therapies for clinical depression.

Additional background art includes U.S. Patent Application No. 2004/0242974; U.S. Pat. Nos. 8,173,695; 6,528,518; Maremmani et al. [*Heroin Add Rel Clin Probl* 8:31-48 (2006)]; and Stanley & Siever [*Am J Psychiatry* 167:24-39 (2010)].

SUMMARY OF THE INVENTION

According to an aspect of some embodiments of the invention, there is provided a method of treating acute suicidality in a subject in need thereof, the method being effected by administering to a subject determined as having acute suicidality a therapeutically effective amount of buprenorphine, or a pharmaceutically acceptable salt thereof.

According to an aspect of some embodiments of the invention, there is provided buprenorphine, or a pharmaceutically acceptable salt thereof, for use in the treatment of acute suicidality in a subject determined as having acute suicidality.

According to an aspect of some embodiments of the invention, there is provided a use of buprenorphine, or a pharmaceutically acceptable salt thereof, in the manufacture of a medicament for treatment of acute suicidality in a subject determined as having acute suicidality.

According to an aspect of some embodiments of the invention, there is provided a method of treating acute suicidality in a subject in need thereof, the method comprising:

(a) determining a presence of acute suicidality in a subject; and (b) administering to a subject determined as having acute suicidality a first therapeutically effective amount of buprenorphine, or a pharmaceutically acceptable salt thereof, during a first time period, the first therapeutically effective amount being less than 0.2 mg per day, and the first time period ranging from 3 days to 3 weeks; and (c) following the first time period, determining a responsiveness of the subject to the first therapeutically effective amount, to thereby determine if the subject is not fully responsive to the first therapeutically effective amount; and (d) if the subject is determined as not fully responsive to the first therapeutically effective amount, administering to the subject, during a second time period, a second therapeutically effective amount of buprenorphine, the second therapeutically effective amount being higher than the first therapeutically effective amount, thereby treating the acute suicidality in a subject in need thereof.

According to an aspect of some embodiments of the invention, there is provided a method of treating acute suicidality in a subject in need thereof, the method comprising:

determining a presence of acute suicidality in a subject; and administering to a subject determined as having acute suicidality a first therapeutically effective amount of buprenorphine, or a pharmaceutically acceptable salt thereof, during a first time period, the first therapeutically effective amount being less than 0.2 mg per day, thereby treating the acute suicidality in a subject in need thereof.

According to an aspect of some embodiments of the invention, there is provided a pharmaceutical composition comprising buprenorphine, or a pharmaceutically acceptable salt thereof, and a pharmaceutically acceptable carrier, the composition being packaged in a packaging material and identified in print, in or on the packaging material, for use in the treatment of acute suicidality in a subject in need thereof.

According to an aspect of some embodiments of the invention, there is provided a pharmaceutical composition unit dosage form comprising buprenorphine, or a pharmaceutically acceptable salt thereof, in an amount of less than 0.2 mg buprenorphine.

According to an aspect of some embodiments of the invention, there is provided buprenorphine, or a pharmaceutically acceptable salt thereof, for use in the treatment of acute suicidality in a subject, wherein the treatment comprises:

(a) determining a presence of acute suicidality in a subject; and (b) administering to a subject determined as having acute suicidality a first therapeutically effective amount of buprenorphine, or a pharmaceutically acceptable salt thereof, during a first time period, the first therapeutically effective amount being less than 0.2 mg per day, and the first time period ranging from 3 days to 3 weeks; and (c) following the first time period, determining a responsiveness of the subject to the first therapeutically effective amount, to thereby determine if the subject is not fully responsive to the first therapeutically effective amount; and (d) if the subject is determined as not fully responsive to the first therapeutically effective amount, administering to the subject, during a second time period, a second therapeutically effective amount of buprenorphine, the second therapeutically effective amount being higher than the first therapeutically effective amount.

According to an aspect of some embodiments of the invention, there is provided buprenorphine, or a pharmaceutically acceptable salt thereof, for use in the treatment of acute suicidality in a subject, wherein the treatment comprises:

determining a presence of acute suicidality in a subject; and administering to a subject determined as having acute suicidality a first therapeutically effective amount of buprenorphine, or a pharmaceutically acceptable salt thereof, during a first time period, the first therapeutically effective amount being less than 0.2 mg per day.

According to an aspect of some embodiments of the invention, there is provided a use of buprenorphine, or a pharmaceutically acceptable salt thereof, in the manufacture of a medicament for treatment of acute suicidality in a subject, wherein the treatment comprises:

(a) determining a presence of acute suicidality in a subject; and (b) administering to a subject determined as having acute suicidality a first therapeutically effective amount of buprenorphine, or a pharmaceutically acceptable salt thereof, during a first time period, the first therapeutically effective amount being less than 0.2 mg per day, and the first time period ranging from 3 days to 3 weeks; and (c) following the first time period, determining a responsiveness of the subject to the first therapeutically effective amount, to thereby determine if the subject is not fully responsive to the first therapeutically effective amount; and (d) if the subject is determined as not fully responsive to the first therapeutically effective amount, administering to the subject, during a second time period, a second therapeutically effective amount of buprenorphine, the second therapeutically effective amount being higher than the first therapeutically effective amount.

According to an aspect of some embodiments of the invention, there is provided a use of buprenorphine, or a pharmaceutically acceptable salt thereof, in the manufacture of a medicament for treatment of acute suicidality in a subject, wherein the treatment comprises:

determining a presence of acute suicidality in a subject; and administering to a subject determined as having acute suicidality a first therapeutically effective amount of buprenorphine, or a pharmaceutically acceptable salt thereof, during a first time period, the first therapeutically effective amount being less than 0.2 mg per day.

According to some embodiments of the invention, the method further comprises, following administering the second therapeutically effective amount of buprenorphine during the second time period:

(e) determining a responsiveness of the subject to the second therapeutically effective amount, to thereby determine if the subject is not fully responsive to the second therapeutically effective amount; and (f) if the subject is determined as not fully responsive to the second therapeutically effective amount, administering to the subject, during a third time period, a third therapeutically effective amount of buprenorphine, the third therapeutically effective amount being higher than the second therapeutically effective amount.

According to some embodiments of the invention, the treatment further comprises, following administering the second therapeutically effective amount of buprenorphine during the second time period:

(e) determining a responsiveness of the subject to the second therapeutically effective amount, to thereby determine if the subject is not fully responsive to the second therapeutically effective amount; and (f) if the subject is determined as not fully responsive to the second therapeutically effective amount, administering to the subject, during a third time period, a third therapeutically effective amount of buprenorphine, the third therapeutically effective amount being higher than the second therapeutically effective amount.

According to some embodiments of the invention, administering buprenorphine is effected for a total time period that ranges from one week to four weeks.

According to some embodiments of the invention, administering buprenorphine is effected until the subject is no longer determined as having acute suicidality.

According to some embodiments of the invention, the treatment comprises administering the buprenorphine to a subject determined as having acute suicidality for a time period that ranges from one week to four weeks.

According to some embodiments of the invention, the treatment comprises administering the buprenorphine to a subject determined as having acute suicidality until the subject is no longer determined as having acute suicidality.

According to some embodiments of the invention, the treatment is effected for a total time period that ranges from one week to four weeks.

According to some embodiments of the invention, the treatment is effected until the subject is no longer determined as having acute suicidality.

According to some embodiments of the invention, the method further comprises, subsequent to the administering, determining a presence of acute suicidality in the subject; and ceasing buprenorphine administration if the subject is no longer determined as having acute suicidality.

According to some embodiments of the invention, the treatment further comprises, subsequent to the administering, determining a presence of acute suicidality in the subject; and ceasing buprenorphine administration if the subject is no longer determined as having acute suicidality.

According to some embodiments of the invention, the administering is effected by a route selected from the group consisting of sublingual administration and transdermal administration.

According to some embodiments of the invention, the administering is effected once per day.

According to some embodiments of the invention, the composition is formulated for an administration selected from the group consisting of sublingual administration and transdermal administration.

According to some embodiments of the invention, the composition is identified for administration once per day.

According to some embodiments of the invention, the buprenorphine or pharmaceutically acceptable salt thereof is formulated for administration by a route selected from the group consisting of sublingual administration and transdermal administration.

According to some embodiments of the invention, the buprenorphine or pharmaceutically acceptable salt thereof is for administration once per day.

According to some embodiments of the invention, the medicament is formulated for administration by a route selected from the group consisting of sublingual administration and transdermal administration.

According to some embodiments of the invention, the medicament is formulated for administration of a therapeutically effective amount of buprenorphine once per day.

According to some embodiments of the invention, the composition comprises a unit dosage form, the unit dosage form comprising a therapeutically effective amount of the buprenorphine or a pharmaceutically acceptable salt thereof.

According to some embodiments of the invention, the treatment comprises:

(a) determining a presence of acute suicidality in a subject; and (b) administering to a subject determined as having acute suicidality one of the unit dosage form per day during a first time period, a unit dosage form described herein comprising less than 0.2 mg of buprenorphine, and the first time period ranging from 3 days to 3 weeks; and (c) following the first time period, determining a responsiveness of the subject to the one unit dosage form per day, to thereby determine if the subject is not fully responsive to the one unit dosage form per day; and (d) if the subject is determined as not fully responsive to the one unit dosage form per day, administering to the subject, during a second time period, two of the unit dosage forms per day, thereby treating the acute suicidality in a subject in need thereof.

According to some embodiments of the invention, the treatment further comprises, following administering two of the unit dosage forms per day during the second time period:

(e) determining a responsiveness of the subject to the two unit dosage forms per day, to thereby determine if the subject is not fully responsive to the two unit dosage forms per day; and (f) if the subject is determined as not fully responsive to the two unit dosage forms per day, administering to the subject, during a third time period, at least three of the unit dosage forms per day.

According to some embodiments of the invention, the According to some embodiments of the invention, the pharmaceutical composition unit dosage form is for use in the treatment of acute suicidality in a subject in need thereof.

According to some embodiments of the invention, the treatment comprises:

(a) determining a presence of acute suicidality in a subject; and (b) administering to a subject determined as having acute suicidality a first therapeutically effective amount of buprenorphine, or a pharmaceutically acceptable salt thereof, during a first time period, the first therapeutically effective amount being less than 0.2 mg per day, and the first time period ranging from 3 days to 3 weeks; and (c) following the first time period, determining a responsiveness of the subject to the first therapeutically effective amount, to thereby determine if the subject is not fully responsive to the first therapeutically effective amount; and (d) if the subject is determined as not fully responsive to the first therapeutically effective amount, administering to the subject, during a second time period, a second therapeutically effective amount of buprenorphine, the second therapeutically effective amount being higher than the first therapeutically effective amount.

According to some embodiments of the invention, administration of the first therapeutically effective amount is effected by administration of one unit dosage form described herein per day.

According to some embodiments of the invention, administration of the second therapeutically effective amount is effected by administration of two unit dosage forms described herein per day.

According to some embodiments of the invention, the treatment further comprises, following administering the second therapeutically effective amount of buprenorphine during the second time period:

(e) determining a responsiveness of the subject to the second therapeutically effective amount, to thereby determine if the subject is not fully responsive to the second therapeutically effective amount; and (f) if the subject is determined as not fully responsive to the second therapeutically effective amount, administering to the subject, during a third time period, a third therapeutically effective amount of buprenorphine, the third therapeutically effective amount being higher than the second therapeutically effective amount.

According to some embodiments of the invention, administration of the third therapeutically effective amount is effected by administration of at least three unit dosage forms described herein per day.

According to some embodiments of the invention, the amount of buprenorphine in the unit dosage form is in a range of from 0.05 to 0.15 mg buprenorphine.

According to some embodiments of the invention, the amount of buprenorphine in the unit dosage form is in a range of from 0.02 to 0.15 mg buprenorphine.

According to some embodiments of the invention, the amount of buprenorphine in the unit dosage form is about 0.1 mg buprenorphine.

According to some embodiments of the invention, the subject is afflicted by a disorder selected from the group consisting of a mood disorder, a personality disorder, a psychosis, a substance abuse disorder, an anxiety disorder, an eating disorder, an attention deficit disorder, a tic disorder, a gender dysphoria, a dissociative disorder, a somatoform disorder, an impulse control disorder and an adjustment disorder.

According to some embodiments of the invention, the subject is afflicted by a disorder selected from the group consisting of a major depressive disorder, anorexia nervosa, a posttraumatic stress disorder, an adjustment disorder, schizophrenia, a borderline personality disorder, a narcissistic personality disorder, an antisocial personality disorder, an intermittent explosive disorder, an attention deficit disorder, a tic disorder, a panic disorder, a body dysmorphic disorder, a dissociative identity disorder, a social anxiety disorder, a substance abuse disorder, a bipolar disorder, and a gender dysphoria.

According to some embodiments of the invention, the subject is not afflicted by a depressive disorder.

According to some embodiments of the invention, the subject is not afflicted by a borderline personality disorder.

According to some embodiments of the invention, the determining comprises measuring suicidality on a scale selected from the group consisting of a Beck Suicidal Ideation (BSI) scale, a Suicide Probability Scale (SPS), a Columbia-Suicide Severity Rating Scale (C-SSRS), and an Overt Aggression Scale Modified (OAS-M).

According to some embodiments of the invention, the determining comprises measuring suicidality on a BSI scale.

According to some embodiments of the invention, the suicidality is characterized by a score of at least 6 on the BSI scale.

According to some embodiments of the invention, the suicidality is characterized by a score of at least 11 on the BSI scale.

According to some embodiments of the invention, the first therapeutically effective amount is in a range of from 0.02 to 0.15 mg per day.

According to some embodiments of the invention, the first therapeutically effective amount is in a range of from 0.05 to 0.1 mg per day.

According to some embodiments of the invention, the second therapeutically effective amount is 0.5 mg per day or less.

According to some embodiments of the invention, the second therapeutically effective amount is at least 0.2 mg per day.

According to some embodiments of the invention, the second therapeutically effective amount is in a range of from 0.1 to 0.3 mg per day.

According to some embodiments of the invention, the second time period ranges from 3 days to 3 weeks.

According to some embodiments of the invention, the third therapeutically effective amount is 0.5 mg per day or less.

According to some embodiments of the invention, the third therapeutically effective amount is at least 0.2 mg per day.

According to some embodiments of the invention, the third therapeutically effective amount is in a range of from 0.2 to 0.5 mg per day.

According to some embodiments of the invention, the third time period ranges from 3 days to 3 weeks.

According to some embodiments of the invention, the therapeutically effective amount is in a range of from 0.02 to 0.5 mg.

According to some embodiments of the invention, the therapeutically effective amount is less than 0.2 mg.

According to some embodiments of the invention, the therapeutically effective amount is in a range of from 0.05 to 0.1 mg.

According to some embodiments of the invention, the therapeutically effective amount is about 0.05 mg.

According to some embodiments of the invention, the therapeutically effective amount is about 0.1 mg.

According to some embodiments of the invention, the therapeutically effective amount is about 0.2 mg.

According to some embodiments of the invention, the therapeutically effective amount is about 0.4 mg.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

* in FIG. 2B indicates t[37]=−2.1, p<0.05, for buprenorphine vs. placebo in change of BSI score from baseline at week 4, LOCF)

DESCRIPTION OF SPECIFIC EMBODIMENTS OF THE INVENTION

The present invention, in some embodiments thereof, relates to therapy and, more particularly, but not exclusively, to methods and compositions for the treatment of acute suicidality.

The principles and operation of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, suicide remains a serious problem, and there is no current effective treatment against acute suicidality. In searching for an effective treatment of acute suicidality, the present inventor has envisioned that acute suicidality can be treated with buprenorphine, an opioid which is sufficiently fast-acting for treatment of acute suicidality, while exhibiting low toxicity and mild withdrawal symptoms. While reducing the present invention to practice, the inventor has uncovered surprising and beneficial effects of low doses (less than 0.2 mg/day) of buprenorphine on levels of suicidality, which allow for the design of particularly effective treatment regimens with minimal adverse side effects (and hence enhanced patient compliance). As exemplified herein, the present inventor has demonstrated that administration of buprenorphine, including administration of low doses of buprenorphine, is capable of reducing suicidality within a short time period, and can therefore serve as an effective agent for treating acute suicidality.

Figure 1:
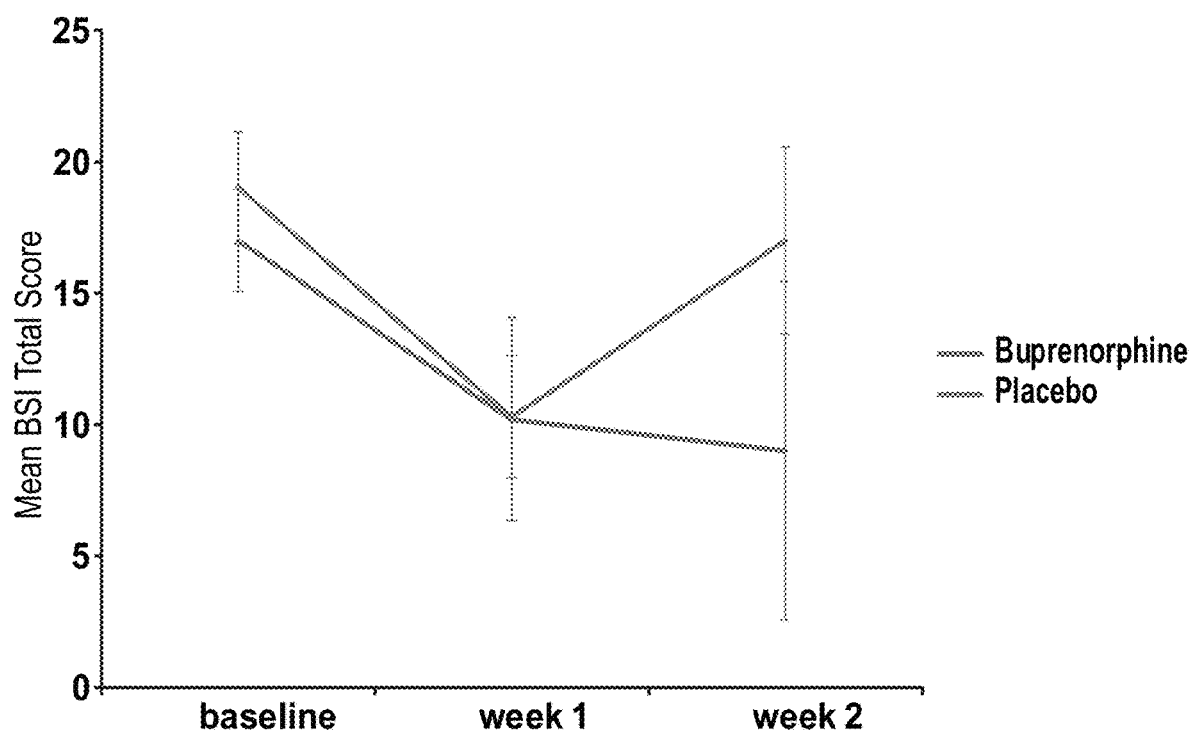
FIG. 1 is a graph showing the effect of treatment for two weeks with buprenorphine (0.2-1.6 mg buprenorphine per day, with the starting dose being 0.2 mg per day, followed by a gradual increase up to the maximal dose during the first week) or placebo on suicidality, as measured by a Beck Suicidal Ideation (BSI) scale for a pilot study, as described in Example 1 herein below.
Figure 2A:
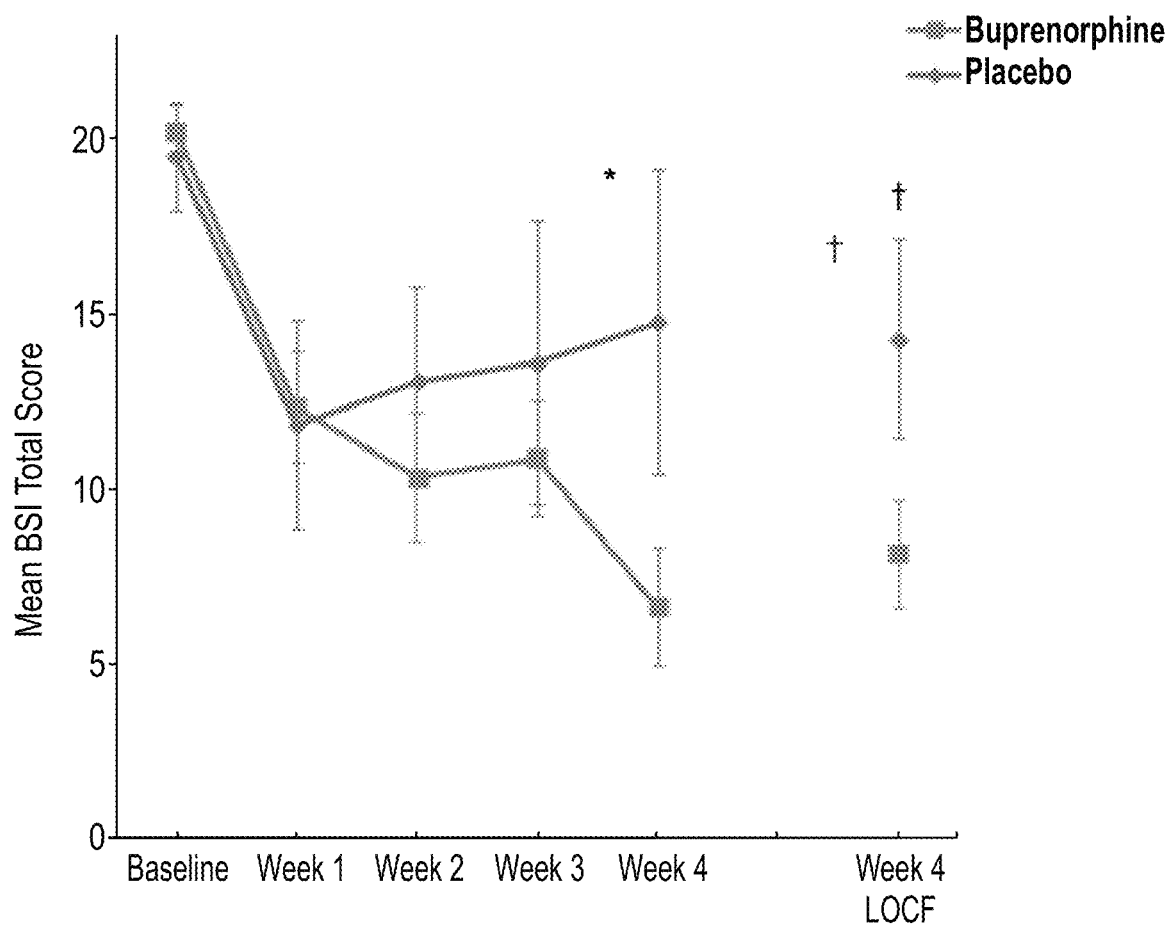
FIGS. 2A and 2B are graphs showing mean BSI (Beck Suicidal Ideation) score (FIG. 2A) and mean change of BSI score relative to baseline (FIG. 2B), as a function of time of treatment with buprenorphine (n=25 at baseline, n=20 at week 4) or placebo (n=14 at baseline, n=9 at week 4), at various doses of buprenorphine and placebo, ranging from 0.1-1.6 mg/day, as described in Example 2 herein below for a clinical study (* in FIG. 2A indicates t[27]=−2.1, p<0.05, for buprenorphine vs. placebo in mean BSI score at week 4), with data for week 4 also presented when calculated by LOCF (last observation carried forward; for buprenorphine, n=25, for placebo n=14, † in FIG. 2A indicates t[37]=−2.1, p<0.05, for buprenorphine vs. placebo in mean BSI score at week 4, LOCF)
Figure 2B:
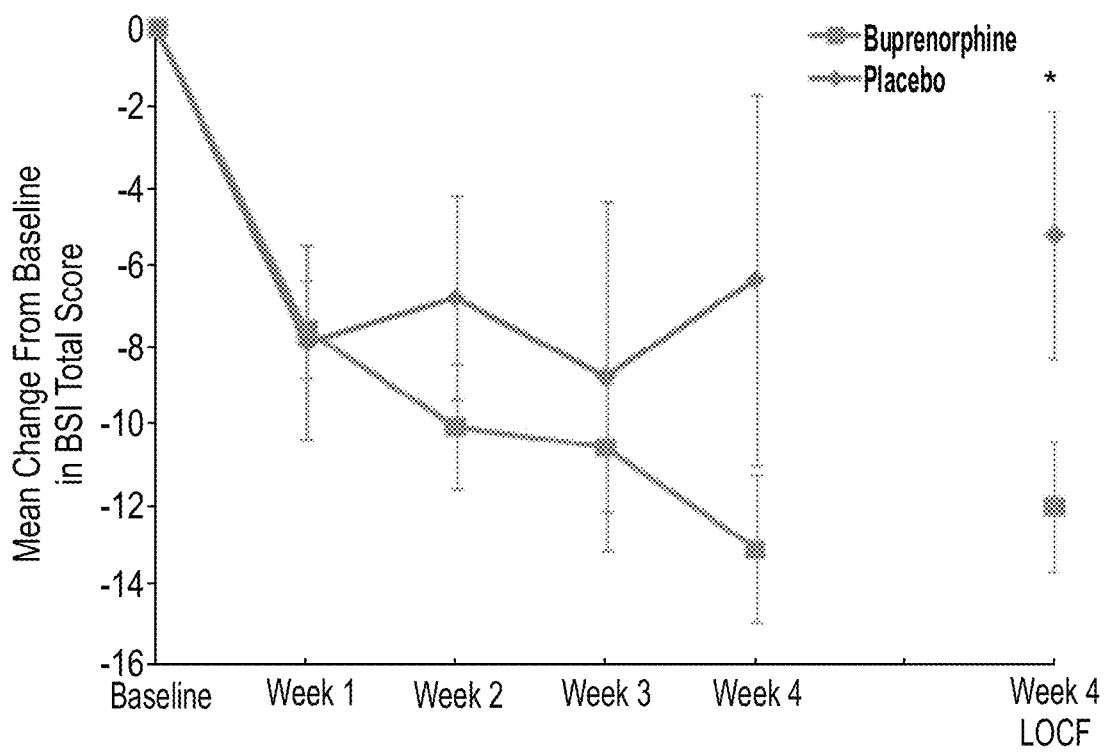
Figure 3:
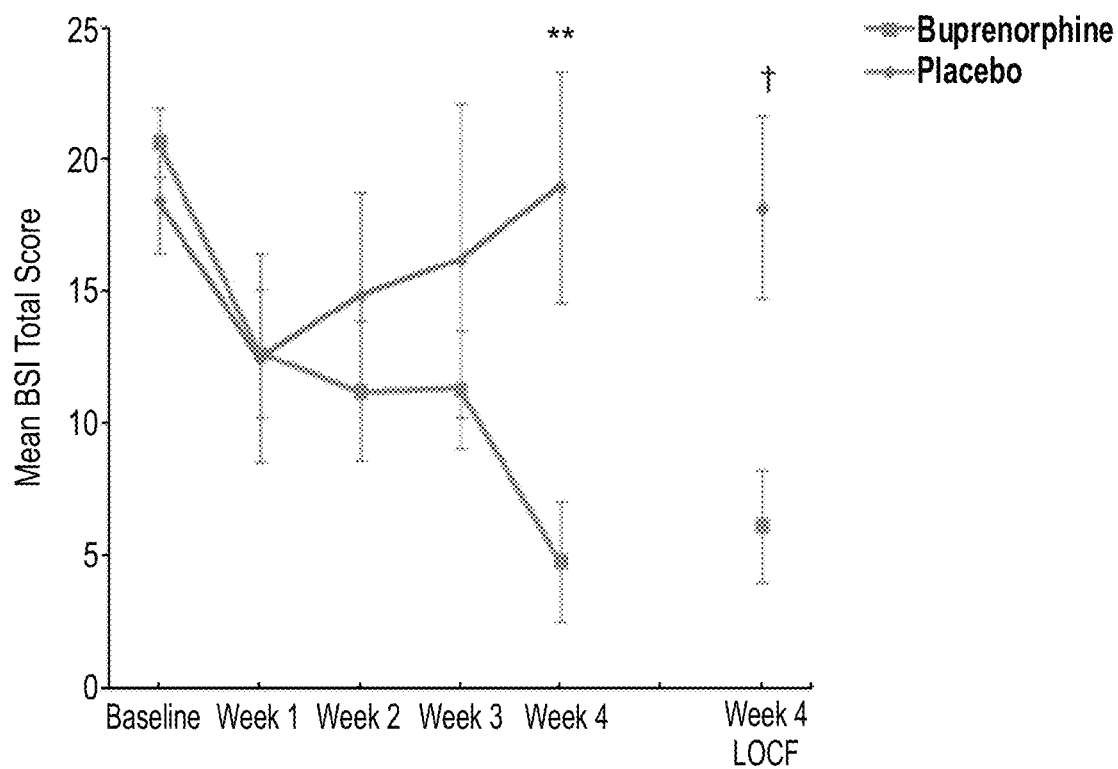
FIG. 3 is a graph showing mean BSI (Beck Suicidal Ideation) score as a function of time of treatment with buprenorphine (n=13 at baseline, n=11 at week 4) or placebo (n=9 at baseline, n=7 at week 4) in subjects who received a dose of 0.4 mg/day or more than 0.4 mg/day (e.g., 0.6, 0.8 or 1.6 mg/day), at week 4 of the clinical study described in Example 2 herein below (** indicates t[16]=−3.2, p<0.01, for buprenorphine vs. placebo); data for week 4 are also presented when calculated by LOCF (last observation carried forward; for buprenorphine, n=13, for placebo n=9, † indicates t[20]=−3.1, p<0.01, for buprenorphine vs. placebo, LOCF)

Referring now to the drawings and tables, FIG. 1 and Table 1 show that administration of buprenorphine (at various doses) for two weeks reduces suicidality. FIGS. 2A and 2B show that suicidality is reduced further by administration of buprenorphine for 4 weeks. FIG. 3 shows that the reduction of suicidality is especially pronounced when the dose of buprenorphine being administered at the end of the 4 week period is 0.4 mg/day or higher. FIGS. 1-3 further show that there is a strong placebo effect in the first week of treatment, and that a clear buprenorphine-specific effect is observed only after the first week of treatment.

Figure 4:
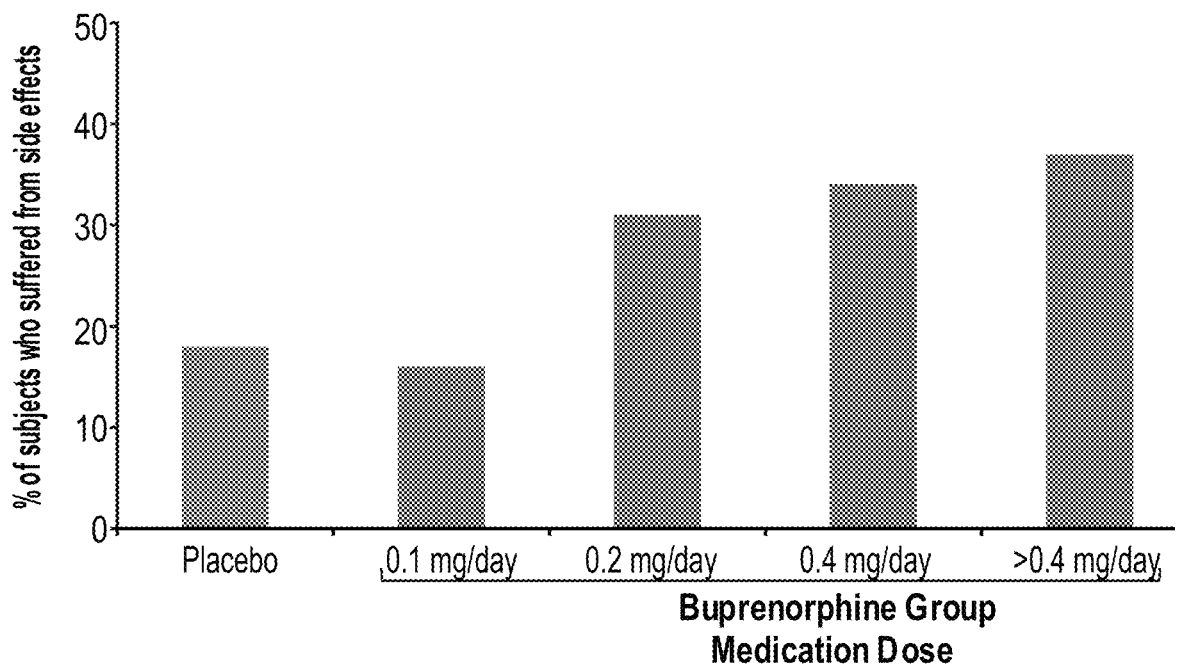
FIG. 4 is a bar graph showing the percentage of subjects who suffered from nausea, vomiting, headache, constipation, dizziness and/or sweating, known to be common side effects of buprenorphine, following treatment during the previous week with 0.1, 0.2, 0.4 or more than 0.4 mg/day (e.g., 0.6, 0.8 or 1.6 mg/day) buprenorphine or with a placebo, as measured in the clinical study described in Example 2 herein below.

FIG. 4 shows that a starting dose of 0.1 mg/day was associated with a lower level of side effects than were starting doses of 0.2 mg/day or more. As described in the Examples section that follows, a starting dose of 0.1 mg/day did not compromise outcome relative to starting doses of 0.2 mg/day or more. These findings indicate that effective treatment of suicidality with buprenorphine can begin with a dose of less than 0.2 mg/day, in order to reduce side effects and enhance patient compliance.

Figure 5:
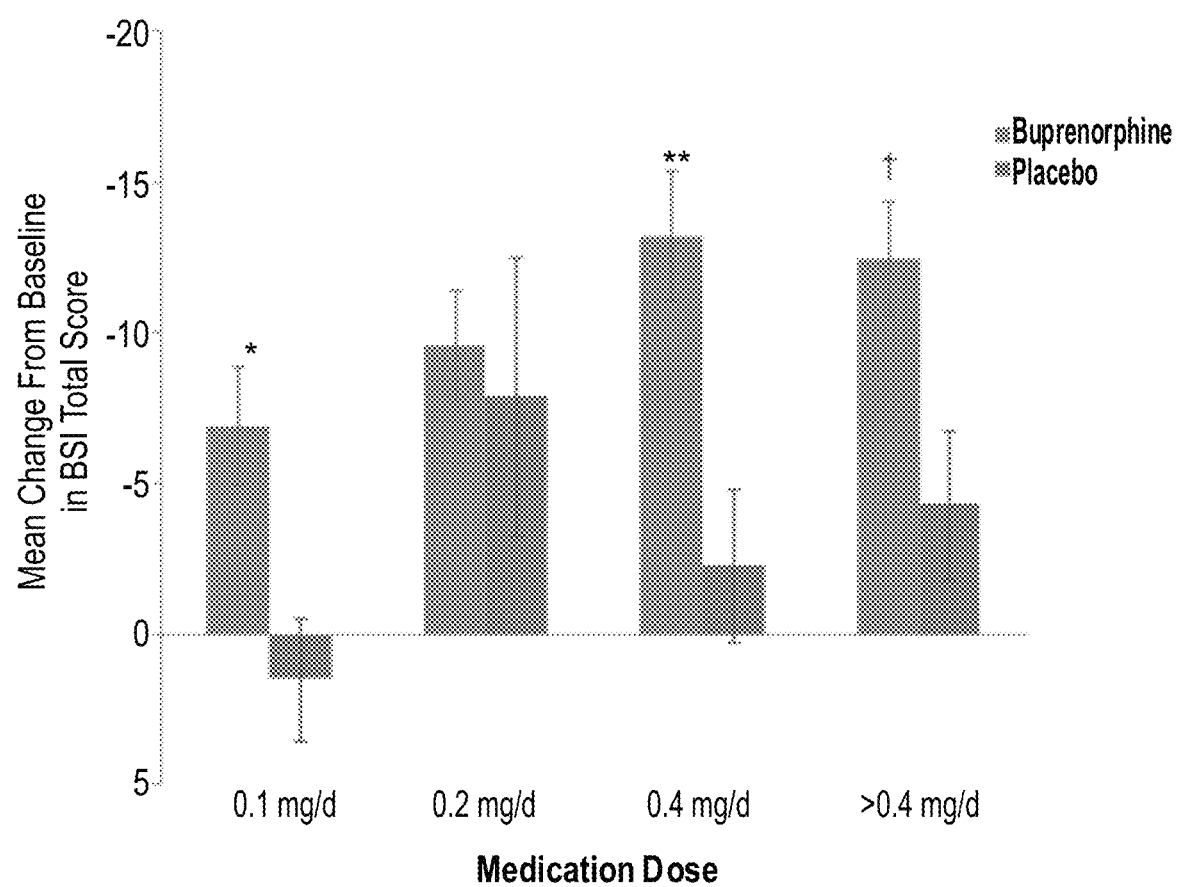
FIG. 5 is a bar graph showing mean change in BSI (Beck Suicidal Ideation) score relative to baseline, following treatment with 0.1, 0.2, 0.4 or more than 0.4 mg/day (e.g., 0.6, 0.8 or 1.6 mg/day) of buprenorphine and placebo, as measured in the clinical study described in Example 2 herein below (for buprenorphine vs. placebo: *$\chi^2$(1, n=14)=−4.43, p<0.05; **$\chi^2$(1, n=20)=6.87, p<0.01; †$\chi^2$(1, n=13)=4.01, p<0.05)
Figure 6A:
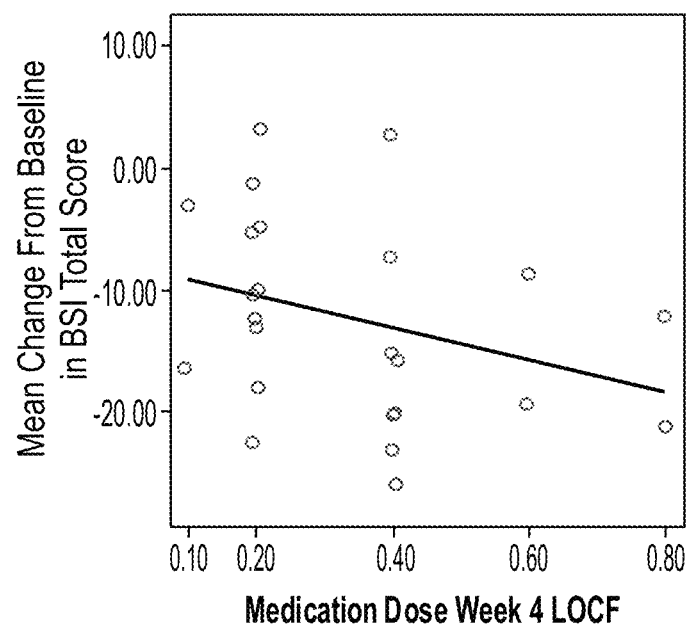
FIGS. 6A and 6B are scatter plots showing changes in BSI (Beck Suicidal Ideation) score relative to baseline as a function of buprenorphine dose (FIG. 6A, n=24) and placebo dose (FIG. 6B, n=12) at week 4 (as calculated by LOCF), as measured in the clinical study described in Example 2 herein below.
Figure 6B:
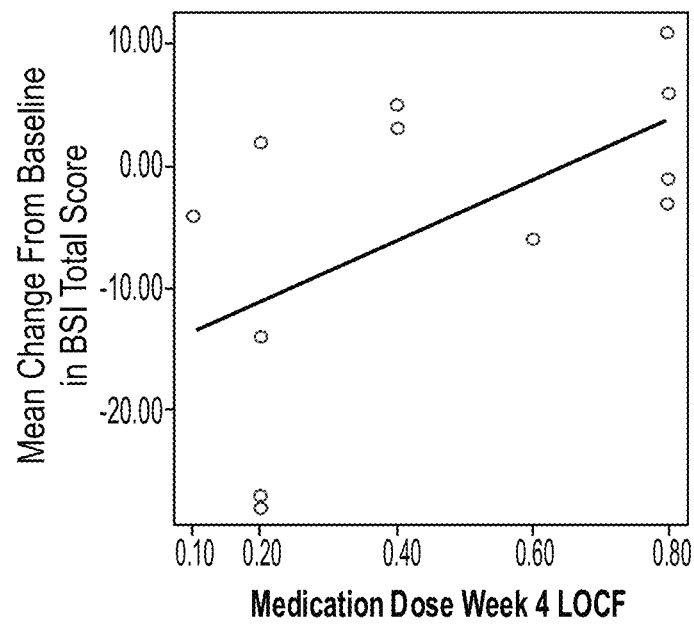

FIG. 5 shows that 0.1 mg/day is effective at reducing suicidality, and that the efficacy of buprenorphine at reducing suicidality is dose-dependent in the range of 0.1 to 0.4 mg/day. FIGS. 6A and 6B show that the reduction in suicidality is correlated to the final buprenorphine dose but inversely correlated to the final placebo dose. These findings indicate that raising the starting dose to a dose of at least 0.2 mg/day may be advantageous in at least some patients, and that doses of more than approximately 0.4 mg/day appear less likely to provide a further benefit.

Figure 7:
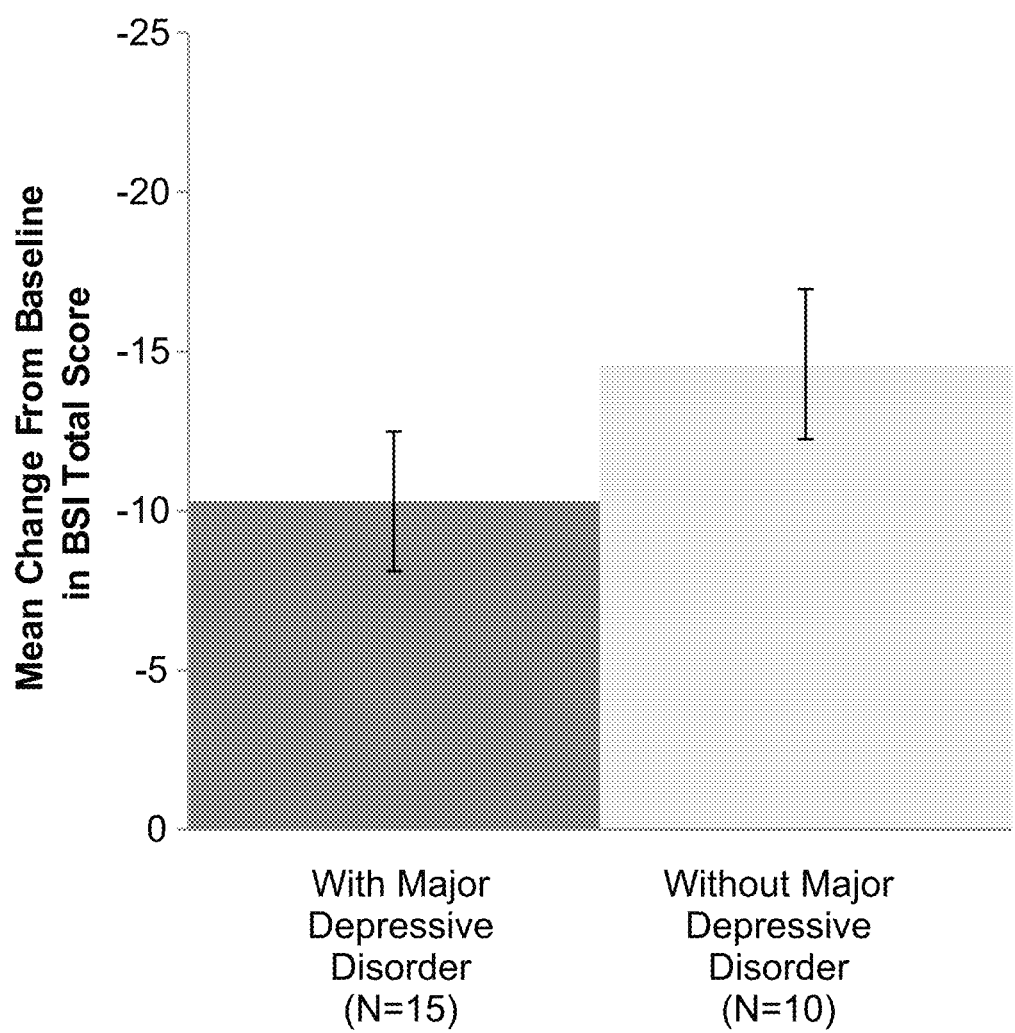
FIG. 7 is a bar graph showing mean change in BSI (Beck Suicidal Ideation) score relative to baseline in subjects with and without major depressive disorder, following treatment in the clinical study described in Example 2 herein below.

FIG. 7 shows that acute suicidality may be treated by buprenorphine in cases where the subject is afflicted with major depressive disorder, as well as in cases where the subject lacks major depressive disorder. Similarly, Table 2 shows that the treatment of acute suicidality by buprenorphine works equally well whether or not the subject is afflicted with an associated disorder or risk factor such as major depressive disorder, personality disorder, and acute axis 4 stressor, and whether or not the subject is under chronic treatment with antidepressants.

Figure 8:
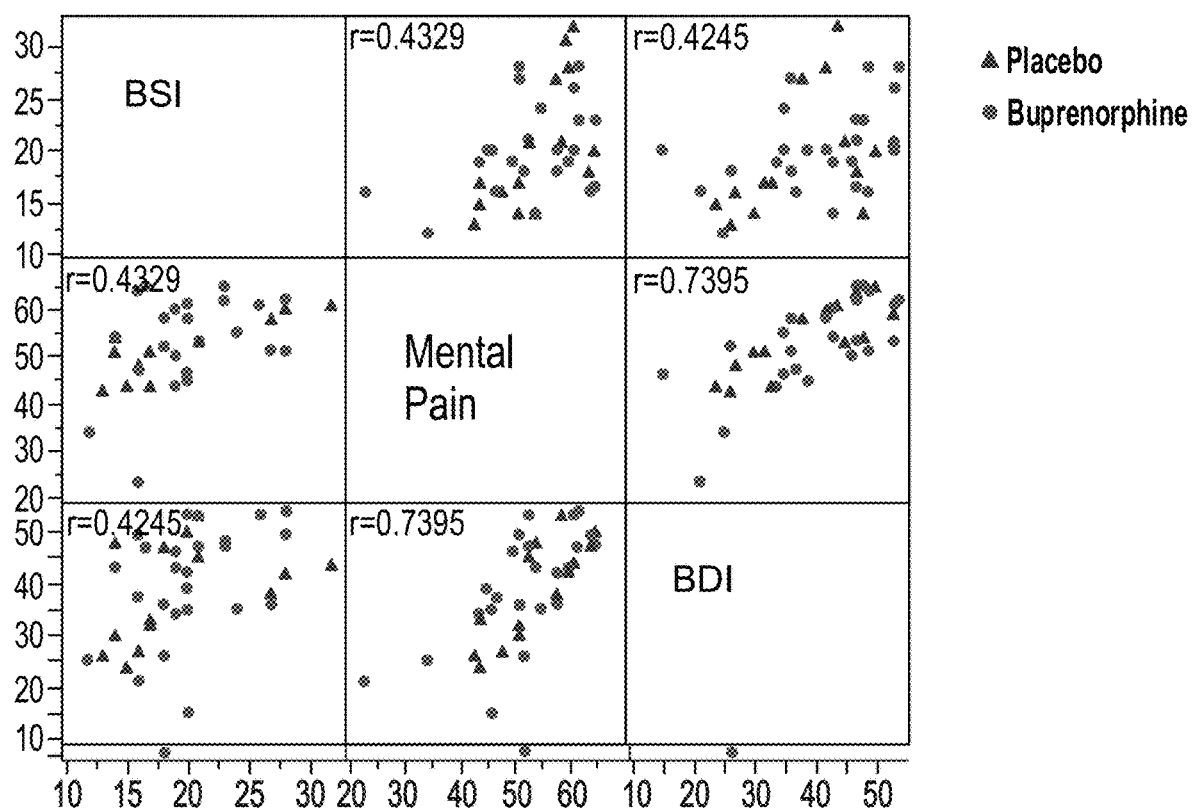
FIG. 8 is a graph presenting scatter plots and Spearman's coefficients (r) showing degree of correlation between any two of BSI (Beck Suicidal Ideation) scores (top row and left column), mental pain scores (middle row and middle column), and BDI (Beck Depression Inventory) scores (bottom row and right column) for all subjects participating in the clinical studies described in Example 2 herein below, at baseline (n=39)
Figure 9:
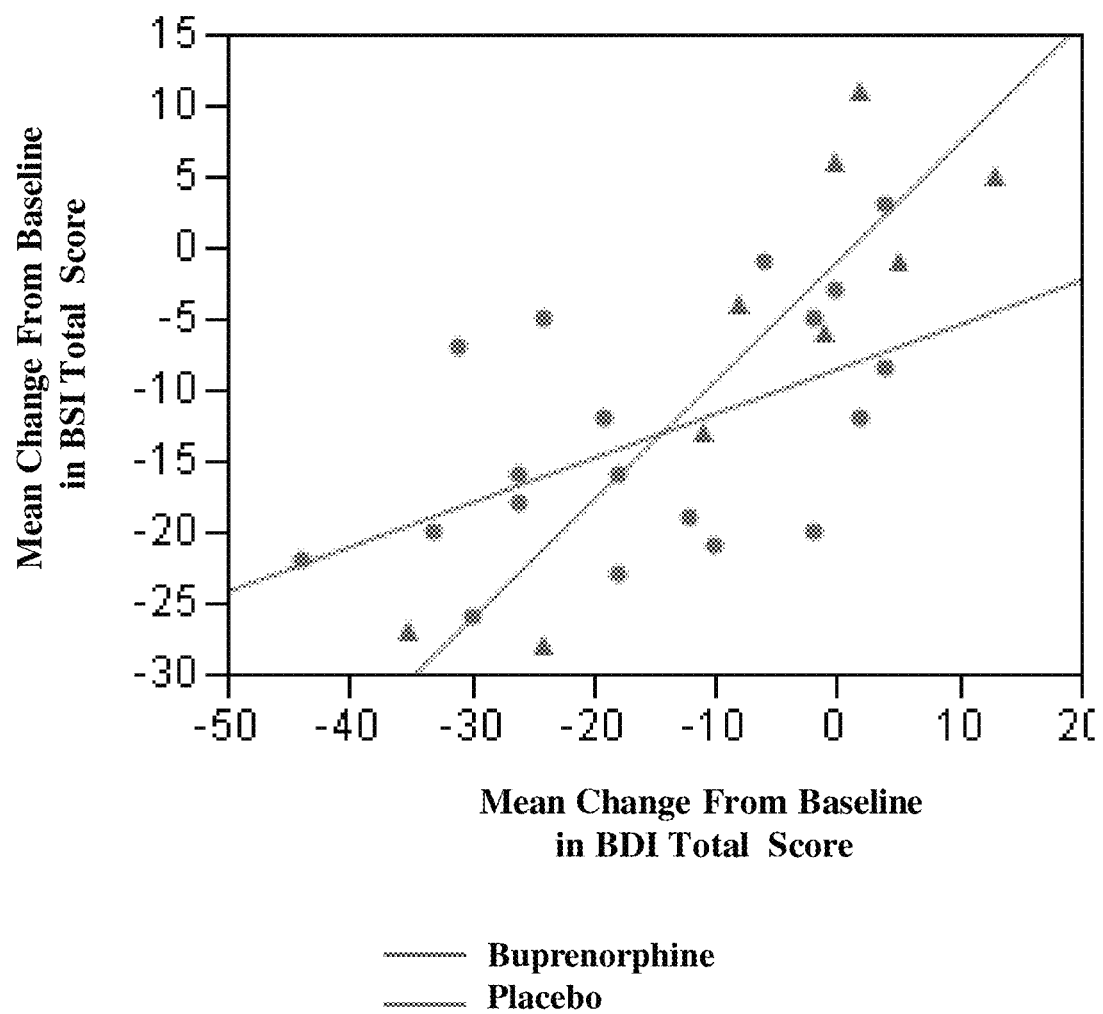
FIG. 9 is a scatter plot showing changes in BSI (Beck Suicidal Ideation) score relative to changes in BDI (Beck Depression Inventory) score, in subjects receiving buprenorphine (circles and less steep trend line, n=25) and placebo (triangles and steeper trend line, n=14) during the clinical study as described in Example 2 herein below.
Figure 10:
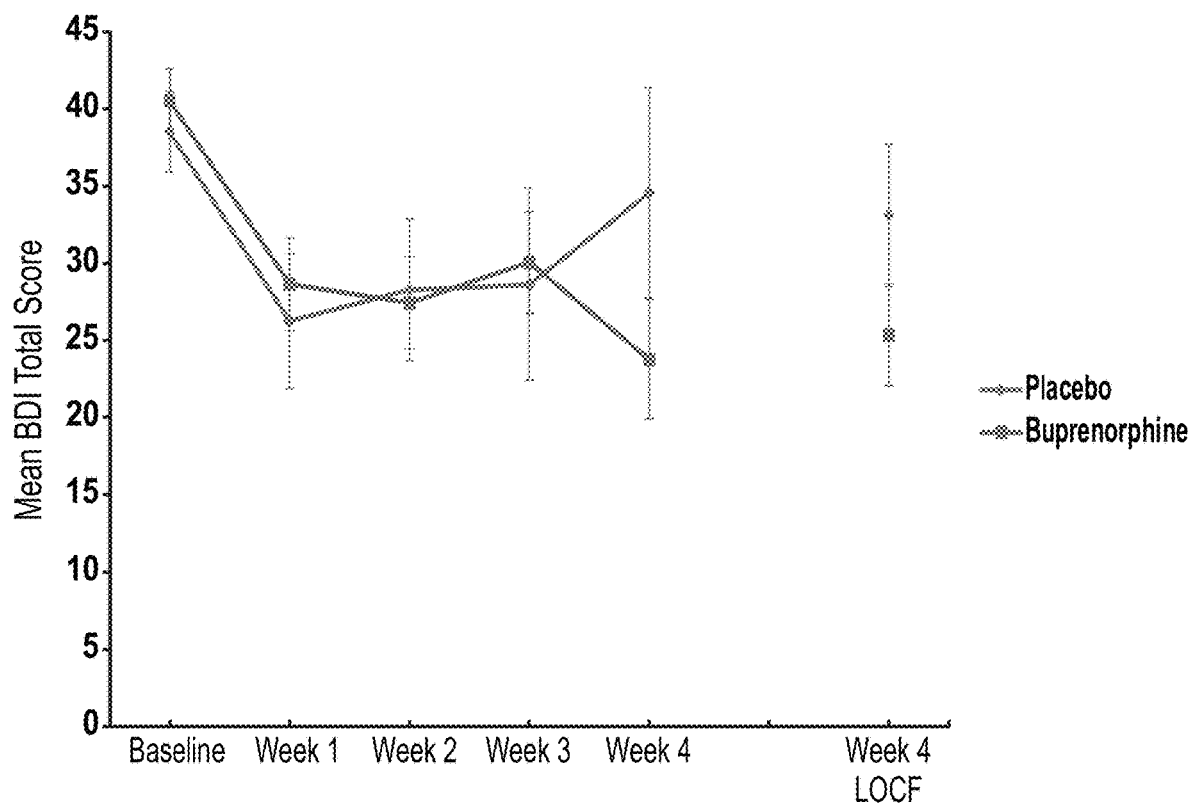
FIG. 10 is a graph showing mean BDI (Beck Depression Inventory) scores, as a function of time of treatment with buprenorphine (n=25 at baseline, n=20 at week 4) or placebo (n=14 at baseline, n=9 at week 4) during the clinical study described in Example 2 herein below; data for week 4 for are also presented when calculated by LOCF (last observation carried forward; for buprenorphine, n=25, for placebo n=14).

FIGS. 8 and 9 show that levels of suicidality during treatment with buprenorphine are relatively independent of a degree of affliction of the subject by depressive symptoms and mental pain. FIG. 9 shows that suicidality and depressive symptoms are more closely linked during treatment with placebo, than during treatment with buprenorphine. FIG. 10 shows that at relatively low doses such as described herein (e.g., less than 0.2 mg/day), the effect of low-dose buprenorphine on depression is limited in comparison with the effect of low-dose buprenorphine on suicidality. These findings indicate that acute suicidality can be treated with buprenorphine as a condition by itself, which is not linked (e.g., as a symptom) to any associated disorder, including depression.

According to an aspect of some embodiments of the present invention there is provided a method of treating acute suicidality in a subject in need thereof, the method being effected by administering to a subject determined as having acute suicidality a therapeutically effective amount of buprenorphine, or a pharmaceutically acceptable salt thereof.

According to another aspect of some embodiments of the present invention there is provided buprenorphine, or a pharmaceutically acceptable salt thereof, for use in the treatment of acute suicidality in a subject determined as having acute suicidality.

According to another aspect of some embodiments of the present invention there is provided a use of buprenorphine, or a pharmaceutically acceptable salt thereof, in the manufacture of a medicament for treatment of acute suicidality in a subject determined as having acute suicidality.

Buprenorphine:

Buprenorphine is a compound having the following chemical structure:

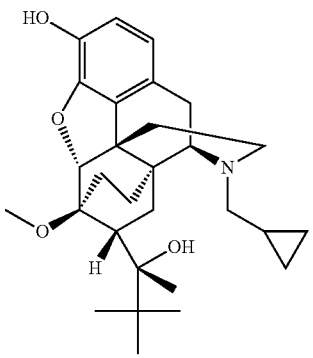 [SMILES: CO[C@@]12CC[C@@]3(C[C@@H]1[C@](C)(O)C(C)(C)C)[C@H]1Cc4ccc(O)c5c4[C@@]3(CCN1CC1CC1)[C@H]2O5]

The systematic (IUPAC) name of buprenorphine is (2S)-2-[(−)-(5R,6R,7R,14S)-9α-cyclopropylmethyl-4,5-epoxy-6,14-ethano-3-hydroxy-6-methoxy morphinan-7-yl]-3,3-dimethylbutan-2-ol ($C_{29}H_{41}NO_4$; CAS number 52485-79-7). The molecular weight of the free base form of buprenorphine (depicted above) is 467.6 grams/mol.

As shown hereinabove, buprenorphine has several chiral centers, and therefore various stereoisomers (e.g., diastereoisomers) of buprenorphine exist. "Buprenorphine" therefore encompasses any of the possible stereoisomers, including any mixture thereof.

According to any of the embodiments described herein, the buprenorphine is substantially in the chiral form depicted hereinabove. Alternatively, the buprenorphine exists as a stereoisomer or enantiomer of the chiral form depicted hereinabove, or as a mixture of two or more chiral forms. It will be appreciated by one of skill in the art that the amount of the compound to be administered must be raised accordingly if an inactive chiral form is present.

"Buprenorphine" further encompass pharmaceutically acceptable salts of buprenorphine and amorphous and crystalline states of buprenorphine or of a salt thereof, including any polymorph thereof.

Herein, the term "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. Examples, without limitation, of pharmaceutically acceptable salts include salts comprising an anion such as a chloride, carboxylate or sulfate anion, and/or a cation such as, but not limited to, ammonium, sodium, potassium and the like. Suitable salts are described in, e.g., Birge et al. [J Pharm Sci 1977, 66:1-19].

A buprenorphine salt may be, for example, a combination of a protonated form of buprenorphine (wherein the amine group thereof is in the form of an ammonium ion) and an anion, which results in an acid addition salt of buprenorphine. The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. An exemplary pharmaceutically acceptable salt of buprenorphine is buprenorphine hydrochloride.

For brevity, the term "buprenorphine" herein refers to both buprenorphine per se (e.g., in free base form) as well as pharmaceutically acceptable salts thereof, except when indicated otherwise.

Herein throughout, and in accordance with common practice in the art, weight amounts of salts of buprenorphine refer to the weight amount of buprenorphine per se (i.e., as the free base). That is, the weight of an acid addition salt is not included in recited weight amounts of buprenorphine, even when the buprenorphine is present as a salt.

Acute Suicidality:

As used herein and in the art, the term "acute" refers to a condition with a relatively short, severe course.

As used herein, the phrase "acute suicidality" refers to a state wherein a subject (e.g., a person) is judged (e.g., by a practitioner such as a psychiatrist) to exhibit an acute risk of suicidality, i.e., a relatively severe risk for suicide in the near future, for example, within a period of 4 weeks. The onset of an acute risk is commonly associated with changes in a subject's circumstances and/or mental state. The acute suicidality may be identified as a condition in its own right or as a symptom of an underlying disorder. Thus, subjects having acute suicidality may suffer only from acute suicidality, or may suffer from a disorder known to be associated with acute suicidality or a disorder which is not associated with acute suicidality, as further discussed in detail hereinafter.

In comparison with an acute risk of suicide, a chronic risk of suicide is a longer-lasting risk, but a less severe risk at any given time. Chronic risk of suicide is commonly associated with a chronic mental illness (e.g., borderline personality disorder, chronic major depressive disorder, or chronic dysthymic disorder) and/or social and demographic factors.

It is to be appreciated that a subject may exhibit both an acute risk for suicide (a severe risk for the near future) and a chronic risk for suicide (a milder, but long-term risk), and the phrase "acute suicidality" is intended to encompass such cases.

In some of the embodiments of any of the aspects of the invention described herein, a method or treatment as described herein is effected by determining a presence of acute suicidality in a subject, and administering the therapeutically effective amount of buprenorphine, or a pharmaceutically acceptable salt thereof, to a subject determined as having acute suicidality.

In some of the embodiments of any of the aspects of the invention described herein, the method or treatment described herein comprises determining a presence of acute suicidality in a subject is done by identifying a recent attempted suicide, a recent declared intent to commit suicide, and/or a recent expressed will to die, wherein a practitioner (e.g., psychiatrist) judges such an attempted suicide, declaration of an intent to commit suicide and/or an expressed will to die to represent a high risk of suicide, as opposed, for example, to a mere attempt to receive attention and/or a part of a long-term but relatively low-risk behavior (e.g., chronic suicidality).

Thus, in some embodiments of any of the aspects of the invention described herein, "a subject determined as having acute suicidality" describes a person who has recently attempted suicide, declared an intent to commit suicide, and/or expressed a will to die, in a manner which a practitioner judges to represent a high risk of suicide, as described herein.

As used herein the term "subject" refers to a human subject determined as having acute suicidality, as described herein. The subject may be male or female, a child or an adult. In exemplary embodiments, the subject is an adult (e.g., at least 18 years old).

In some embodiments of any of the aspects of the invention described herein, determining a presence of acute suicidality in a subject (e.g., as part of a method or treatment described herein) is done using a test for measuring suicidality according to any technique used in the art.

In some embodiments, the test comprises a questionnaire filled out by a subject.

Examples of tests for measuring suicidality include, without limitation, a Beck Suicidal Ideation (BSI) scale (as described in Beck & Steer [*Manual for the Beck Scale for Suicide Ideation*. San Antonio, Tex.: Psychological Corporation (1991)]); a Suicide Probability Scale (SPS) (as described in Cull & Gill [*Suicide Probability Scale Manual*. Los Angeles, Calif. (1988)]); a Columbia-Suicide Severity Rating Scale (C-SSRS) (as described in Posner et al. [*CNS Spectr,* 12:156-162 (2007)]); and an Overt Aggression Scale Modified (OAS-M) (as described in Coccaro et al. [*J Neuropsychiatry Clin Neurosci,* 3:S44-51 (1991)]). Such tests comprise a questionnaire, wherein the answers to the questionnaire can be quantified to obtain value on a scale.

According to some embodiments of any of the aspects of the invention described herein, determining suicidality (e.g., as part of a method or treatment described herein) comprises measuring suicidality on a BSI scale. For example, suicidality is optionally characterized by a score of at least 4, at least 5, at least 6, at least 7, at least 8, at least 9, at least 10, at least 11, at least 12, at least 13, at least 14, or at least 15 on a BSI scale. For this example, a subject that scores at least 4, at least 5, at least 6, at least 7, at least 8, at least 9, at least 10, at least 11, at least 12, at least 13, at least 14, or at least 15 on a BSI scale, is determined as a subject having acute suicidality.

In some embodiments, suicidality is determined when a subject's score is at least 4, least 5, at least 6, at least 7, at least 8, at least 9, at least 10, at least 11, at least 12, at least 13, at least 14, or at least 15 on a BSI scale.

The acute suicidality may be determined according to a passive aspect of suicidality (e.g., a will to not be alive), an active aspect of suicidality (e.g., the active will to commit suicide), and/or a specific aspect of suicidality (e.g., potential lethality and the degree of concreteness of specific plans to commit suicide). As will be apparent to the skilled practitioner, tests for determining suicidality as described herein (e.g., a BSI scale) evaluate different aspects of suicidality, with different portions of the test evaluating different aspects of suicidality. Hence, each aspect may be determined according to the results of an appropriate portion of a test for suicidality.

The active and specific aspects of suicidality, and the specific aspect of suicidality in particular, may be the most clinically important factors in determining a risk of suicide.

Hence, in some embodiments, suicidality is determined by evaluating an active and/or specific aspect of suicidality in a subject.

In some embodiments, suicidality is determined by evaluating a specific aspect of suicidality in a subject.

According to some embodiments of any of the aspects of the invention described herein, suicidality is determined by more than one criterion (e.g., as part of a method or treatment described herein).

For example, criteria for determining a presence of acute suicidality for beginning buprenorphine treatment may optionally be different than the criteria for determining when to cease buprenorphine treatment. In some embodiments, for example, the criteria for ending treatment are stricter than the criteria for beginning treatment.

Thus, for example, while in some embodiments, a subject scoring at least 11 on a BSI scale is determined as having acute suicidality and hence is administered with buprenorphine, in some embodiments, buprenorphine administration to this subject is continued until the subject scores no more than 10 on a BSI scale, optionally no more than 9, optionally no more than 8, optionally no more than 7, optionally no more than 6, optionally no more than 5, and optionally no more than 4 on a BSI scale.

In addition, while in some embodiments, a subject scoring at least 6 on a BSI scale is determined as having acute suicidality and hence is administered with buprenorphine, in some embodiments, buprenorphine administration to this subject is continued until the subject scores no more than 5 on a BSI scale, optionally no more than 4, and optionally no more than 3 on a BSI scale.

In some embodiments of any of the aspects of the invention described herein, the buprenorphine is administered to a subject identified as having acute suicidality but not afflicted by psychache at a level which is clinically significant. Such a subject would be unlikely to respond to a treatment directed at reducing psychache.

In some embodiments, the method or treatment according to embodiments of any of the aspects of the invention described herein further comprises determining a level of psychache in the subject, in order to determine whether the subject exhibits a clinically significant degree of psychache.

The psychache may be characterized by a method known in the art. Examples of suitable scales for measuring psychache include, for example, a Holden Psychache Scale (PAS) [Holden et al., *Canadian J Behav Sci*, 33:224-232 (2001)] and an Orbach and Mikulincer Mental Pain (OMMP) scale) [Orbach et al., *Suicide Life Threat Behav*, 33:231-241 (2003)]. In some embodiments, a clinically significant level of psychache is characterized by a score of at least 24, optionally at least 27, optionally at least 30, optionally at least 33, optionally at least 36, optionally at least 39, optionally at least 42, optionally at least 45, optionally at least 48, optionally at least 51, and optionally at least 54, on the PAS scale.

In some embodiments of any of the aspects of the invention described herein, the buprenorphine is administered to a subject identified as having both acute suicidality and being afflicted psychache at a clinically significant level (e.g., as described herein).

In some embodiments of any of the aspects of the invention described herein, treatment of a subject afflicted by psychache as described herein is continued when the subject exhibits either acute suicidality or psychache above a pre-determined level (e.g., according to criteria described herein). That is, an aim of the treatment is to reduce both suicidality and psychache.

In some embodiments of any of the aspects of the invention described herein, treatment of a suicidality associated with psychache is continued when the subject exhibits both acute suicidality and psychache above a pre-determined level (e.g., according to criteria described herein).

According to some embodiments of any of the aspects of the invention described herein, the subject being treated according to any method or treatment described herein may not suffer from a medical condition or disorder (e.g., a psychiatric condition or disorder) other than acute suicidality. Thus, in some embodiments, the acute suicidality being treated is recognized as a disorder by itself, and, in some embodiments, the acute suicidality being treated is not associated with any other medical condition or disorder.

In some embodiments of any of the aspects of the invention described herein, the subject being treated according to any method or treatment described herein is afflicted by a medical condition or disorder associated with the acute suicidality.

Thus, the subject being treated according to the present embodiments, may be a subject having a medical condition or disorder other than acute suicidality.

For example, the subject may be afflicted by a condition associated with an identifiable external event, for example, a psychological trauma. In some embodiments, the subject is afflicted by a recent psychological trauma, for example, a trauma which has occurred one month or less, optionally one week or less, and optionally 24 hours or less before the appearance of symptoms of acute suicidality. Posttraumatic stress disorder, as described herein, is an example of a disorder associated with an external event.

Herein, the phrase "psychological trauma" refers to an event which is, at least temporarily, psychologically stressful and/or life-threatening for a subject. It is emphasized that such an event does not necessarily have to satisfy criterion A of the DSM-IV definition of Posttraumatic Stress Disorder, or criterion A of the DSM-IV definition of Acute Stress Disorder.

The subject may be afflicted by a condition associated with a use of a chemical substance, for example, a psychoactive substance. The acute suicidality may be associated either with a direct biological effect of the substance and/or with withdrawal symptoms caused when the subject ceases (permanently or temporarily) using the substance. Examples of substances which may be associated with acute suicidality include, but are not limited to, alcohol, amphetamines, opioids (e.g., heroin), cocaine (particularly during withdrawal), nicotine and benzodiazepines.

Thus, in some embodiments, the subject being treated according to any of the embodiments of a method or treatment as described herein is a subject that consumes a chemical substance as described herein.

In some embodiments, the subject being treated according to any of the embodiments of a method or treatment as described herein is a subject that has ceased consumption of a chemical substance as described herein.

Alternatively, the subject may be afflicted by a medical condition or disorder which has no evident association with any identifiable external event and/or substance abuse. Such a condition or disorder may be due to genetic factors, environmental factors and/or random chance, although it may be difficult or impossible to determine which.

Exemplary conditions or disorders with which a subject having acute suicidality may be further afflicted (according to any of the embodiments described herein) include, but are not limited to, a mood disorder, a personality disorder, a psychosis, a substance abuse disorder, an anxiety disorder, an eating disorder, an attention deficit disorder, a tic disorder, a gender dysphoria, a dissociative disorder, a somatoform disorder, an impulse control disorder and an adjustment disorder. An adjustment disorder is an exemplary disorder in a subject having acute suicidality.

Thus, in some embodiments, the subject being treated by the method or treatment as described herein is a subject having one or more of the above-listed conditions or disorders.

Herein, a "mood disorder" refers to a disorder where a disturbance in a person's mood is considered to be the main underlying feature, as determined by DSM-IV criteria. Examples of mood disorders which may be associated with acute suicidality include, but are not limited to, a depressive disorder (including major depressive disorder, dysthymic disorder, and depressive disorder not otherwise specified) and a bipolar disorder (including bipolar disorder and cyclothymic disorder).

Herein, a "personality disorder" refers to an Axis II disorder according to DSM-IV criteria, the disorder being associated with a person's personality type and/or behavior. Typically, a personality disorder is associated with severe disturbances in behavior, which are generally associated with considerable personal and social disruption. Examples of personality disorders which may be associated with acute suicidality include, but are not limited to, a borderline personality disorder (characterized by unusual levels of instability in mood and black and white thinking), a narcissistic personality disorder (characterized by excessive preoccupation with issues of personal adequacy, power, prestige and vanity), and an antisocial personality disorder (characterized by a pervasive pattern of disregard for, and violation of, the rights of others).

Herein, a "psychosis" refers to a mental state involving a gross deficit in reality testing. Schizophrenia is a non-limiting example of psychosis which may be associated with acute suicidality.

Herein, a "substance abuse disorder" encompasses both "substance abuse" and "substance dependence", as these conditions are determined by DSM-IV criteria.

Herein, an "anxiety disorder" refers to disorder associated with an abnormal and pathological fear and/or anxiety, as determined according to DSM-IV criteria. Examples of anxiety disorders which may be associated with acute suicidality include, but are not limited to, a social anxiety disorder (characterized by an intense fear of social situations, causing distress and impaired ability to function in at least some parts of daily life), a panic disorder (characterized by recurring severe panic attacks), a posttraumatic stress disorder (characterized by re-experiencing a traumatic event to which a subject has been exposed, for more than one month).

Herein, an "eating disorder" refers to a condition defined by abnormal eating habits, including either insufficient or excessive food intake, to the detriment of the individual's physical and/or mental health, as determined according to DSM-IV criteria. Anorexia nervosa is a non-limiting example of an eating disorder which may be associated with acute suicidality.

Herein, an "attention deficit disorder" refers to the disorder "ADHD predominantly inattentive", as defined by DSM-IV criteria, which is characterized by inattention, easy distractibility, disorganization, procrastination, forgetfulness and lethargy-fatigue.

Herein, a "tic disorder" refers to a disorder characterized by tics (sudden, rapid, non-rhythmic, stereotyped, involuntary movements), as defined by DSM-IV criteria.

Herein, a "gender dysphoria" refers to a disorder (also known in the art as "gender identity disorder") defined, in accordance with DSM-IV criteria, by discontent of a person with his/her biological sex and/or the gender they were assigned at birth.

Herein, a "dissociative disorder" refers to a condition that involves disruptions or breakdowns of memory, awareness, identity and/or perception, as determined according to DSM-IV criteria. A dissociative identity disorder, characterized by a person displaying multiple distinct identities or personalities (each with its own pattern of perceiving and/or interacting with the environment), is a non-limiting example of a dissociative disorder which may be associated with acute suicidality.

Herein, a "somatoform disorder" refers to a mental disorder characterized, in accordance with DSM-IV criteria, by physical symptoms that suggest physical illness or injury, wherein the symptoms cannot be explained fully by a general medical condition, direct effect of a substance, or attributable to another mental disorder (e.g. panic disorder). Body dysmorphic disorder (characterized by excessive concern and preoccupation with a perceived defect in one's physical features) is a non-limiting example of a somatoform disorder which may be associated with acute suicidality.

Herein, an "impulse control disorder" refers to a mental disorder characterized, according to DSM-IV criteria, by a failure to resist an impulsive act or behavior that may be harmful to self or others. Intermittent explosive disorder (characterized by an inability to control violent impulses) is a non-limiting example of an impulse control disorder which may be associated with acute suicidality.

Herein, an "adjustment disorder" refers to a psychological response to an identifiable stressor or group of stressors that cause significant emotional or behavioral symptoms, as determined according to DSM-IV criteria.

In some embodiments of any of the aspects of the invention described herein, the subject is afflicted by with one or more of the following disorders (such that the subject being treated has one or more of the following disorders): a major depressive disorder, anorexia nervosa, a posttraumatic stress disorder, an adjustment disorder, schizophrenia, a borderline personality disorder, a narcissistic personality disorder, an antisocial personality disorder, an intermittent explosive disorder, an attention deficit disorder, a tic disorder, a panic disorder, a body dysmorphic disorder, a dissociative identity disorder, a social anxiety disorder, a substance abuse disorder, a bipolar disorder, and a gender dysphoria.

In some embodiments, the disorder is a mood disorder, and the mood disorder is a major depressive disorder.

In some embodiments, the disorder is a mood disorder, and the mood disorder is a dysthymic disorder.

In some embodiments, the disorder is a mood disorder, and the mood disorder is a bipolar disorder.

In some embodiments, the disorder is an eating disorder, and the eating disorder is anorexia nervosa.

In some embodiments, the disorder is an anxiety disorder, and the anxiety disorder is a posttraumatic stress disorder.

In some embodiments, the disorder is an anxiety disorder, and the anxiety disorder is a social anxiety disorder.

In some embodiments, the disorder is an anxiety disorder, and the anxiety disorder is a panic disorder.

In some embodiments, the disorder is a personality disorder, and the personality disorder is a borderline personality disorder.

In some embodiments, the disorder is a personality disorder, and the personality disorder is a narcissistic personality disorder.

In some embodiments, the disorder is a personality disorder, and the personality disorder is an antisocial personality disorder.

In some embodiments, the disorder is a psychosis, and the psychosis is schizophrenia.

In some embodiments, the disorder is a somatoform disorder, and the somatoform disorder is a body dysmorphic disorder.

In some embodiments, the disorder is an impulse control disorder, and the impulse control disorder is an intermittent explosive disorder.

In some embodiments, the disorder is a dissociative disorder, and the dissociative disorder is a dissociative identity disorder.

In some embodiments, the disorder presents acute symptoms (e.g., acute episodes of acute anxiety, impulsivity, depression, and/or mania) which are associated with the acute suicidality.

In some embodiments, the disorder presents chronic symptoms (e.g., chronic anxiety, impulsivity, depression, and/or mania) which are acutely exacerbated for any reason (e.g., changes in a subject's circumstances and/or mental state and/or medication regimen), resulting in the acute suicidality.

Thus, in some embodiments, the subject being treated can be a subject afflicted by any of the above-listed conditions or disorders.

In some embodiments, the administration of buprenorphine to treat the subject according to a method or treatment described herein according to any aspect of the invention is made in conjunction with administering to the subject an additional agent for treating the medical condition or disorder.

When the medical condition or disorder is chronic, co-treatment of a chronic condition or disorder with buprenorphine and the additional agent may optionally be a short-term treatment as described herein (e.g., for four weeks or less), wherein the chronic condition or disorder is then treated in the long-term by administration of the additional agent alone (i.e., without buprenorphine).

In some embodiments, co-treatment with buprenorphine and the additional agent is a long-term treatment (e.g., for at least 5 years, at least 10 years), and optionally a permanent treatment (i.e., for life), so as to prevent recurrence of acute suicidality.

As discussed and exemplified herein, the efficacy of buprenorphine in treating suicidality does not rely on an antidepressant effect of buprenorphine. That is, a reduction in acute suicidality may occur in subjects even in the absence of a corresponding decrease in depression and/or in subjects in which acute suicidality is not caused by depression. Consequently, in some embodiments, the method or treatment described herein according to any aspect of the invention can be used to treat suicidality in a subject not afflicted by a depression.

Thus, in some embodiments, the subject is afflicted by a psychological disorder other than a depressive disorder (e.g., a psychological disorder described herein).

In some embodiments, the subject is afflicted by a psychological disorder other than a mood disorder (e.g., a psychological disorder described herein).

In some embodiments, the subject is not afflicted by a depressive disorder (e.g., major depressive disorder).

In some embodiments, the subject is not afflicted by a mood disorder.

Determination whether a subject has a mood disorder and/or a depressive disorder (e.g., major depressive disorder) can be made according to DSM-IV diagnostic criteria.

For example, a subject determined as having an acute suicidality on a BSI scale as described herein, does not meet DSM-IV criteria for a mood disorder and hence is not considered as having a mood disorder.

In some embodiments, the subject exhibiting acute suicidality does exhibit a mood disorder as described herein (e.g., a depressive disorder), but buprenorphine treatment according to a method or treatment described herein does not cause any clinically significant changes in symptoms of the mood disorder, even when acute suicidality has been successfully treated (by reduction or elimination of acute suicidality).

For example, a subject determined as having an acute suicidality on a BSI scale as described herein, does meet DSM-IV criteria for a mood disorder (e.g., a depressive disorder) and hence is identified as having a mood disorder (e.g., a depressive disorder). However, in such embodiments, buprenorphine treatment does not cause any clinically significant changes in symptoms of the mood disorder, such that the subject still meets DSM-IV criteria for the mood disorder, even after treatment of the acute suicidality.

Thus, buprenorphine treatment for a limited period of time (e.g., 4 weeks or less) as described herein for any aspect of the invention described herein may result in a subject in which acute suicidality has been considerably decreased or even eliminated, while the subject continues to exhibit symptoms of a mood disorder (e.g., depression). In some such embodiments, the subject is further treated with an antidepressant or any other suitable medication known in the art for treating the symptoms of the mood disorder. In some such embodiments, the subject is further treated with buprenorphine, in order to treat the mood disorder (e.g., depression).

In some embodiments, the subject is afflicted by a psychological disorder other than a borderline personality disorder (e.g., a psychological disorder described herein).

In some embodiments, the subject is afflicted by a psychological disorder other than a personality disorder (e.g., a psychological disorder described herein).

In some embodiments, the subject is not afflicted by a borderline personality disorder.

In some embodiments, the subject is not afflicted by a personality disorder.

Determination whether a subject has a personality disorder and/or a borderline personality disorder is according to DSM-IV diagnostic criteria.

For example, a subject determined as having an acute suicidality on a BSI scale as described herein, does not meet DSM-IV criteria for a personality disorder (e.g., a borderline personality disorder) and hence is not identified as having a personality disorder (e.g., a borderline personality disorder).

In some embodiments, the subject exhibiting acute suicidality does exhibit a personality disorder as described herein (e.g., a borderline personality disorder), but buprenorphine treatment according to a method or treatment described herein does not cause any clinically significant changes in symptoms of the personality disorder, even when acute suicidality has been successfully treated (by reduction or elimination of acute suicidality).

Thus, buprenorphine treatment for a limited period of time (e.g., 4 weeks or less) as described herein may result in a subject in which acute suicidality has been considerably decreased or even eliminated, while the subject continues to exhibit symptoms of a personality disorder.

For example, a subject determined as having an acute suicidality on a BSI scale as described herein, does meet DSM-IV criteria for a personality disorder (e.g., a borderline personality disorder) and hence is identified as having a personality disorder (e.g., a borderline personality disorder). However, in such embodiments, buprenorphine treatment according to a method or treatment described herein does not cause any clinically significant changes in symptoms of the mood disorder, such that the subject still meets DSM-IV criteria for the personality disorder, even after treatment of the acute suicidality.

In some embodiments, the subject is afflicted by a psychological disorder other than a depressive disorder and a borderline personality disorder (e.g., a psychological disorder described herein).

In some embodiments, the subject is afflicted by a psychological disorder other than a mood disorder and a personality disorder (e.g., a psychological disorder described herein).

In some embodiments, the subject is not afflicted by either a depressive disorder (e.g., major depressive disorder) or a borderline personality disorder.

Thus, in some embodiments, the subject being treated according to embodiments of any aspects of the present invention, is afflicted by one or more conditions or disorders such as, but not limited to, anorexia nervosa, a posttraumatic stress disorder, an adjustment disorder, schizophrenia, a narcissistic personality disorder, an antisocial personality disorder, an intermittent explosive disorder, an attention deficit disorder, a tic disorder, a panic disorder, a body dysmorphic disorder, a dissociative identity disorder, a social anxiety disorder, a substance abuse disorder, a bipolar disorder, and a gender dysphoria, wherein the aforementioned conditions or disorders respond to the buprenorphine administration. In some embodiments, the subject being treated has, or is characterized as having, one or more of anorexia nervosa, a posttraumatic stress disorder, an adjustment disorder, schizophrenia, a narcissistic personality disorder, an antisocial personality disorder, an intermittent explosive disorder, an attention deficit disorder, a tic disorder, a panic disorder, a body dysmorphic disorder, a dissociative identity disorder, a social anxiety disorder, a substance abuse disorder, a bipolar disorder, and a gender dysphoria, as described herein. In some embodiments, the subject is not afflicted by any psychological disorder other than the aforementioned disorders.

In some embodiments, the subject is not afflicted by either a mood disorder or a personality disorder.

According to optional embodiments, the subject being treated according to embodiments of any aspects of the present invention is afflicted by one or more conditions or disorders such as, but not limited to, a psychosis, a substance abuse disorder, an anxiety disorder, an eating disorder, an attention deficit disorder, a tic disorder, a gender dysphoria, a dissociative disorder, a somatoform disorder, an impulse control disorder and an adjustment disorder, wherein the aforementioned conditions or disorders respond to the buprenorphine administration.

In some embodiments, the subject being treated has, or is characterized as having, one or more of a psychosis, a substance abuse disorder, an anxiety disorder, an eating disorder, an attention deficit disorder, a tic disorder, a gender dysphoria, a dissociative disorder, a somatoform disorder, an impulse control disorder, and an adjustment disorder, as described herein. In some embodiments, the subject is not afflicted by any psychological disorder other than the aforementioned disorders.

It is to be appreciated that buprenorphine treatment of acute suicidality according to some embodiments of the invention differs from the use of buprenorphine to treat opioid abuse and/or dependency, in that treatment of acute suicidality utilizes significantly lower dosages of buprenorphine.

Thus, in embodiments wherein the subject is afflicted by a condition associated with a substance abuse disorder (optionally a substance abuse disorder associated with opioid abuse and/or dependency), the treatment of suicidality, according to any embodiments described herein, is optionally effected using a dosage of less than 2 mg per day, such as described herein, optionally 1.6 mg per day or less, optionally 1.2 mg per day or less, optionally 1 mg per day or less, optionally less than 0.8 mg per day, optionally less than 0.6 mg per day, optionally less than 0.4 mg per day, and optionally less than 0.2 mg per day, as described herein.

In some embodiments, the subject is afflicted by a psychological disorder other than a substance abuse disorder associated with opioid abuse and/or dependency (e.g., a psychological disorder described herein). In some embodiments, the subject is afflicted by a psychological disorder other than a substance abuse disorder (any kind of substance abuse disorder).

In some embodiments, the subject is not afflicted by a substance abuse disorder associated with opioid abuse and/or dependency. In some embodiments, the subject is not afflicted by any kind of substance abuse disorder.

Determination whether a subject has a substance abuse disorder and/or a substance abuse disorder associated with opioid abuse and/or dependency is according to DSM-IV diagnostic criteria.

For example, a subject determined as having an acute suicidality on a BSI scale as described herein, does not meet DSM-IV criteria for a substance abuse disorder and hence is not identified as having a substance abuse disorder.

In some embodiments, the subject exhibiting acute suicidality does exhibit a substance abuse disorder as described herein (e.g., a substance abuse disorder associated with opioid abuse and/or dependency), but buprenorphine treatment according to embodiments of any aspects of the invention does not cause any clinically significant changes in symptoms of the substance disorder, even when acute suicidality has been successfully treated (by reduction or elimination of acute suicidality).

Thus, buprenorphine treatment for a limited period of time (e.g., 4 weeks or less) as described herein may result in a subject in which acute suicidality has been considerably decreased or even eliminated, while the subject continues to exhibit symptoms of a substance abuse disorder.

For example, a subject determined as having an acute suicidality on a BSI scale as described herein, does meet DSM-IV criteria for a substance abuse disorder and hence is identified as having a substance abuse disorder. However, in such embodiments, buprenorphine treatment does not cause any clinically significant changes in symptoms of the substance abuse disorder, such that the subject still meets DSM-IV criteria for the substance abuse disorder, even after treatment of the acute suicidality.

As discussed herein, in some embodiments of various aspects of the invention described herein, the method or treatment comprises determining a responsiveness of the subject to a therapeutically effective amount of buprenorphine (e.g., the first therapeutically effective amount), to determine if the subject is not fully responsive to the therapeutically effective amount of buprenorphine.

Herein, the terms "responsive" and "responsiveness" refer to a therapeutically beneficial effect, such as a reduction in suicidality, in the subject in response to administration of the buprenorphine.

Herein, a subject is considered "fully responsive" if the response achieves a desired effect. A subject who is not fully responsive may be a subject in which no substantial response was observed (e.g., administration of the given amount of buprenorphine had no therapeutic effect) or a subject in which a response was observed, but the desired effect was not achieved (e.g., the therapeutic effect was too small), e.g., as described in more detail herein.

A subject determined to be unlikely to tolerate a dosage higher than a given therapeutically effective amount of buprenorphine (e.g., based on observed adverse side effects) is considered herein to be fully responsive to the therapeutically effective amount. In such a case, administering a higher amount of buprenorphine is expected to result in an inferior outcome (e.g., due to adverse side effects) such that the therapeutically effective amount (a lower dosage) is considered to be best (for that particular subject) for achieving the desired effect obtainable by administering buprenorphine In some embodiments, a desired effect in the context of a method or treatment described herein is determined by a practitioner for an administered amount of buprenorphine based on the experimental results described herein.

In some embodiment, determining a responsiveness comprises measuring suicidality as described herein (e.g., using a BSI scale).

In some embodiments, a subject is fully responsive if a level of suicidality in the subject is below a certain threshold level.

In some embodiments, a threshold level is determined according to time since initiation of administration of treatment. Thus, for example, different threshold levels for full responsiveness may be determined for one week after initiation of treatment, two weeks after initiation of treatment, three weeks after initiation of treatment, and so forth.

In some embodiments, the threshold level for full responsiveness is relative to a level of suicidality prior to treatment (e.g., the threshold is a specific decrease in a score measuring suicidality).

In some embodiments, the threshold is determined by a decrease in BSI score relative to a BSI score prior to administration of buprenorphine.

In some embodiments, the threshold for one week after initiation of treatment is at least 4 in a BSI score. In some embodiments, the threshold for one week after initiation of treatment is at least 5. In some embodiments, the threshold for one week after initiation of treatment is at least 6. In some embodiments, the threshold for one week after initiation of treatment is at least 7. In some embodiments, the threshold for one week after initiation of treatment is at least 8. In some embodiments, the threshold for one week after initiation of treatment is at least 9. In some embodiments, the threshold for one week after initiation of treatment is at least 10.

In some embodiments, the threshold for two weeks after initiation of treatment is at least 6 in a BSI score. In some embodiments, the threshold for one week after initiation of treatment is at least 7. In some embodiments, the threshold for one week after initiation of treatment is at least 8. In some embodiments, the threshold for one week after initiation of treatment is at least 9. In some embodiments, the threshold for one week after initiation of treatment is at least 10. In some embodiments, the threshold for one week after initiation of treatment is at least 11. In some embodiments, the threshold for one week after initiation of treatment is at least 12.

In some embodiments, the threshold for three weeks after initiation of treatment is at least 8 in a BSI score. In some embodiments, the threshold for one week after initiation of treatment is at least 9. In some embodiments, the threshold for one week after initiation of treatment is at least 10. In some embodiments, the threshold for one week after initiation of treatment is at least 11. In some embodiments, the threshold for one week after initiation of treatment is at least 12. In some embodiments, the threshold for one week after initiation of treatment is at least 13. In some embodiments, the threshold for one week after initiation of treatment is at least 14.

In some embodiments, the threshold level for full responsiveness is absolute (e.g., the threshold is a specific score measuring suicidality).

In some embodiments, the threshold is determined by a BSI score.

In some embodiments, the threshold for one week after initiation of treatment is a BSI score of no more than 16. In some embodiments, the threshold for one week after initiation of treatment is a BSI score of no more than 15. In some embodiments, the threshold for one week after initiation of treatment is a BSI score of no more than 14. In some embodiments, the threshold for one week after initiation of treatment is a BSI score of no more than 13. In some embodiments, the threshold for one week after initiation of treatment is a BSI score of no more than 12. In some embodiments, the threshold for one week after initiation of treatment is a BSI score of no more than 11. In some embodiments, the threshold for one week after initiation of treatment is a BSI score of no more than 10.

In some embodiments, the threshold for two weeks after initiation of treatment is a BSI score of no more than 14. In some embodiments, the threshold for one week after initiation of treatment is a BSI score of no more than 13. In some embodiments, the threshold for one week after initiation of treatment is a BSI score of no more than 12. In some embodiments, the threshold for one week after initiation of treatment is a BSI score of no more than 11. In some embodiments, the threshold for one week after initiation of treatment is a BSI score of no more than 10. In some embodiments, the threshold for one week after initiation of treatment is a BSI score of no more than 9. In some embodiments, the threshold for one week after initiation of treatment is a BSI score of no more than 8.

In some embodiments, the threshold for three weeks after initiation of treatment is a BSI score of no more than 12. In some embodiments, the threshold for one week after initiation of treatment is a BSI score of no more than 11. In some embodiments, the threshold for one week after initiation of treatment is a BSI score of no more than 10. In some embodiments, the threshold for one week after initiation of treatment is a BSI score of no more than 9. In some embodiments, the threshold for one week after initiation of treatment is a BSI score of no more than 8. In some embodiments, the threshold for one week after initiation of treatment is a BSI score of no more than 7. In some embodiments, the threshold for one week after initiation of treatment is a BSI score of no more than 6.

In some embodiments, a subject is fully responsive if a level of suicidality in the subject decreases at a rate (e.g., an average rate over a given time period) which is at least a certain threshold rate.

In some embodiments, the threshold rate is based on a BSI scale. In some embodiments, the threshold rate is at least 1 per week on a BSI scale. In some embodiments, the threshold rate is at least 2 per week on a BSI scale. In some embodiments, the threshold rate is at least 3 per week on a BSI scale. In some embodiments, the threshold rate is at least 4 per week on a BSI scale. In some embodiments, the threshold rate is at least 5 per week on a BSI scale. In some embodiments, the threshold rate is at least 6 per week on a BSI scale. In some embodiments, the threshold rate is at least 7 per week on a BSI scale. In some embodiments, the threshold rate is at least 8 per week on a BSI scale. In some embodiments, the threshold rate is at least 9 per week on a BSI scale. In some embodiments, the threshold rate is at least 10 per week on a BSI scale.

It is to be appreciated that the phrase "per week on a BSI scale" is not intended to refer necessarily to a period of time lasting one week. Thus, a decrease at a rate of "7 per week on a BSI scale" has the same meaning as a decrease at a rate of 1 per day on a BSI scale.

In some embodiments, the threshold rate is calculated based on a previously determined level of suicidality (e.g., a level determined at the beginning of administration of a given amount of buprenorphine), a predetermined target level of suicidality, and a predetermined period of time remaining to reach the target level of suicidality. In such embodiments, the threshold rate is a rate which is sufficient to decrease a level of suicidality from the previously determined level of suicidality to the target level within the predetermined period of time. Thus, full responsiveness in a subject starting with a relatively moderate level of suicidality may involve a lower rate of decrease in suicidality levels than full responsiveness in a subject starting with a relatively high level of suicidality.

In some embodiments, the predetermined target level of suicidality is a level wherein the subject is no longer determined as having acute suicidality (e.g., as described herein).

In some embodiments, a predetermined period of time remaining to reach the target level of suicidality is at least one week. In some embodiments, a predetermined period of time remaining to reach the target level of suicidality is at least two weeks. In some embodiments, a predetermined period of time remaining to reach the target level of suicidality is at least three weeks. In some embodiments, a predetermined period of time remaining to reach the target level of suicidality is at least four weeks.

In some embodiments, treatment is scheduled to be finished by a predetermined time after initiation of administration of a therapeutically effective amount of buprenorphine (as described herein), and the predetermined period of time remaining to reach the target level of suicidality is the time remaining until the treatment is scheduled to be finished. Thus, for example, if the treatment is scheduled to end four weeks after initiation of treatment, and administration of a second therapeutically effective amount is administered during a second time period (as described herein) beginning from two weeks after initiation of treatment, then a predetermined period of time remaining to reach the target level of suicidality may be calculated as being two weeks.

In some embodiments, in order to determine responsiveness to a therapeutically effective amount of buprenorphine, the abovementioned previously determined level of suicidality is determined when administration of the therapeutically effective amount is initiated, or at least as close to initiation as is practical.

A threshold rate for determining responsiveness may optionally be calculated using any suitable scale for determining suicidality (e.g., as described herein). In some embodiments, the scale is a BSI scale.

In some embodiments, the threshold rate is calculated based on an assumption of linear decrease in a level of suicidality upon administration of a therapeutically effective amount of buprenorphine.

In some embodiments, the threshold rate is calculated based on an assumption of an exponential decrease in a level of suicidality upon administration of a therapeutically effective amount of buprenorphine.

In some embodiments, full responsiveness is based, at least in part, on the impressions and/or opinion of an attending physician (e.g., psychiatrist) and/or policy of a physician or institution responsible for the safety of the subject, rather than on strict quantitative calculations.

Dosing and Regimen:

Herein, a "therapeutically effective amount" generally means an amount of an ingredient effective to treat, alleviate or ameliorate a disorder or a symptom, or prolong the survival of the subject being treated. In the context of embodiments of the present invention, which relate to an amount effective to treat acute suicidality, the phrase "therapeutically effective amount" describes an amount of buprenorphine which is sufficient to alleviate acute suicidality and reduce the acute risk of suicide.

It is to be appreciated that what constitutes a therapeutically effective amount may vary over different situations. For example, as exemplified herein, a placebo may be highly effective at first for treating, alleviating or ameliorating suicidality, but ineffective after a period of approximately one week. Hence, any small amount of buprenorphine (including zero) is considered herein to be a therapeutically effective amount when a placebo is effective, but not when a placebo is ineffective.

According to some embodiments of any of the aspects of the invention described herein, a therapeutically effective amount described herein (e.g., a first therapeutically effective amount, a second therapeutically effective amount, a third therapeutically effective amount, and so forth, as described herein) of buprenorphine to be administered is 5 mg per day or less.

In some embodiments, the therapeutically effective amount is 0.2 mg/day or less. In some embodiments, the therapeutically effective amount is less than 0.2 mg/day.

As exemplified herein, daily dosages of above about 0.4 mg per day may have little or no additional benefits, and may increase side effects.

Hence, according to some embodiments, a therapeutically effective amount (e.g., a first therapeutically effective amount, a second therapeutically effective amount, a third therapeutically effective amount, and so forth) of buprenorphine to be administered is 0.5 mg per day or less. In some embodiments, the therapeutically effective amount is 0.4 mg per day or less. In some embodiments, the therapeutically effective amount is 0.3 mg per day or less. In some embodiments, the therapeutically effective amount is 0.2 mg per day or less.

In some embodiments, the therapeutically effective amount is at least 0.01 mg per day, optionally in a range of from 0.01 to 0.5 mg per day. In some embodiments, the therapeutically effective amount is at least 0.02 mg per day, optionally in a range of from 0.03 to 0.5 mg per day. In some embodiments, the therapeutically effective amount is at least 0.01 mg per day, optionally in a range of from 0.04 to 0.5 mg per day. In some embodiments, the therapeutically effective amount is at least 0.01 mg per day, optionally in a range of from 0.05 to 0.5 mg per day.

According to some embodiments of any of the aspects of the invention described herein, administration is effected by sublingual administration or transdermal administration.

Without being bound by any particular theory, it is believed that routes such as sublingual administration and transdermal administration are advantageous in that they avoid extensive first-pass metabolism of buprenorphine in the liver (as typically occurs upon oral administration) while being relatively convenient and easy to perform (e.g., in comparison with injection).

In some embodiments, a daily dosage of buprenorphine (e.g., as part of any method or treatment described herein) is given in a single administration, such that administration is effected once per day (e.g., in the form of one or more sublingual dosage forms). Administration once per day may be effected during the whole course of treatment, or during a portion of the treatment period, for example, during a portion of the treatment wherein the daily dosage is relatively low (e.g., less than 0.2 mg/day). In some embodiments, administration is effected in the morning. In some embodiment, administration is effected in the evening (or at night).

Without being bound by any particular theory it is believed that administration in the evening results in less adverse side effects than administration in the morning. It is further believed that administration of buprenorphine in the morning may result in a stronger therapeutic effect of the buprenorphine administration (e.g., greater reduction in suicidality) of an equal amount of buprenorphine in the evening.

Thus, a timing of administration (e.g., in the morning or the evening) is optionally selected according to the needs of a patient (e.g., as assessed by an attending physician) at a given time, for example, whether it is more important to reduce side effects or to enhance a reduction in suicidality.

In alternative embodiments, a daily dosage of buprenorphine (e.g., as part of any method or treatment described herein) is divided among a plurality of administrations. In some embodiments, administration is effected twice per day (e.g., wherein each administration comprises half a daily dosage described herein). In some embodiments, administration is effected three times per day (e.g., wherein each administration comprises a third of a daily dosage described herein).

In some embodiments of any of the aspects of the invention described herein, buprenorphine is administered in a continuous manner, for example, continuous transdermal administration (e.g., via a transdermal patch) or subcutaneous administration (e.g., an injectable sustained release matrix).

Continuous administration may optionally last for 1 day or less, wherein a daily dosage of buprenorphine (e.g., as described herein) is administered during that time.

Alternatively, continuous administration may last for more than one day, for example at least 2 days, at least 3 days, at least 4 days, at least 5 days, at least 6 days, and even at least 7 days. In such embodiments, a daily dosage described herein refers to an average dosage administered per day during the continuous administration. In some embodiments, the daily dosage is administered each day during the continuous administration.

The time period of a continuous administration may be controlled by selecting a suitable rate of release of buprenorphine from a formulation (e.g., a formulation for transdermal administration, such as a transdermal patch, or a formulation for subcutaneous administration, such as an injectable sustained release matrix, as described herein), in combination with a suitable total amount of buprenorphine in the formulation.

The above-described dosages of buprenorphine are particularly suitable for administration by sublingual and transdermal routes, for which the bioavailability of buprenorphine is approximately 40%.

In some embodiments of any of the aspects of the invention described herein, the above-described dosages are modified so as to account for the bioavailability for a particular route. Thus, for example, for injection and infusion, wherein bioavailability is about 100%, a therapeutically effective amount of buprenorphine may be 40% of a dosage described hereinabove (e.g., 0.2 mg per day or less rather than 0.5 mg per day or less, 0.04 mg per day or less rather than 0.1 mg per day or less).

In some embodiments, the treatment of acute suicidality according to any of the aspects of the invention described herein is characterized as "acute", namely, as being a short-term treatment that is ceased once the patient is no longer determined as having acute suicidality, as described herein.

Thus, in some embodiments, a method or treatment described herein further comprises, subsequent to administering buprenorphine, determining a presence of acute suicidality in the subject, and ceasing buprenorphine administration if the subject is no longer determined as having acute suicidality.

Determining that a subject no longer has acute suicidality can be made using any of the above-described methodologies. As indicated hereinabove, a criterion for determining acute suicidality prior to ceasing buprenorphine administration may be stricter than a criterion for determining a subject as having acute suicidality. In some embodiments, a subject is determined as no longer having acute suicidality if he scores no more than 10, no more than 9, no more than 8, no more than 7, no more than 6, no more than 5, no more than 4, or no more than 3 on a BSI scale.

As a treatment for an acute condition, the total time period for administration of buprenorphine is a limited period of time, such as 4 weeks or less, optionally 3 weeks or less, optionally two weeks or less, and optionally one week or less.

As used herein, the phrase "total time period" encompasses all time periods described herein for administration of a therapeutically effective amount, for example, a first time period, a second time period, a third time period, a fourth time period, a fifth time period.

Treatment of acute suicidality for a brief period of time (e.g., 4 weeks or less) is advantageous because it both serves a previously unmet need for an effective and rapidly acting treatment for suicidal patients (as treatments such as anti-depressant therapy and psychotherapy are generally not effective in a short-term period), while minimizing the potential risk of abuse of buprenorphine. The potential risk of buprenorphine abuse has been a major obstacle to the widespread use of buprenorphine, due, among other reasons, to the strong anti-narcotic bias among the professional and lay communities in the U.S. [Callaway, *Biol Psychiatry* 39:989-990 (1996)].

In some embodiments, administration according a method or treatment described herein is for a total time period of at least two weeks (e.g., from 2 to 4 weeks). In some embodiments, administration is for a total time period of at least three weeks (e.g., a time period in a range of from 3 to 4 weeks). Without being bound by any particular theory, it is believed that such treatment periods minimize the risk of acute suicidality returning after the end of treatment, which may be more likely to happen after briefer treatment periods.

In some embodiments, administration of buprenorphine according a method or treatment described herein is effected until the subject is determined as no longer having acute suicidality. Thus, the subject no longer expresses an intent to commit suicide and/or a will to die, and/or the subject no longer has acute suicidality as determined according to a test described herein. In some embodiments, the subject no longer exhibits symptoms (e.g., anxiety, depression, and/or substance abuse) of a medical condition or disorder (e.g., a disorder as described herein) associated with the acute suicidality.

The method or treatment of treating acute suicidality according to any aspect of the invention described herein is optionally effected in combination with an additional therapy known in the art, such as antidepressant therapy and/or psychotherapy, which is effective over a relatively long period of time (e.g., more than one month). In this manner, the buprenorphine may be used to treat acute suicidality while the additional therapy is used, for example, to treat a long-term disorder associated with the acute suicidality or to handle any other cause that lead to the acute suicidality, as described herein.

According to some embodiments of any of the aspects of the invention described herein, the method or treatment described herein is effected by administering to the subject a first therapeutically effective amount of buprenorphine for a first time period, and further comprises, following the first time period, determining a responsiveness of the subject to the first therapeutically effective amount, to thereby determine if the subject is not fully responsive (as described herein) to the first therapeutically effective amount. If the subject is determined as not fully responsive, the method or treatment further comprises administering to the subject, during a second time period, a second therapeutically effective amount, which is higher than the first therapeutically effective amount, that is, the amount of buprenorphine to be administered is increased.

In some embodiments, the stages of determining responsiveness (in a method or treatment as described herein) and, if appropriate, increasing an amount of buprenorphine to be administered, are repeated. That is, the method or treatment further comprises, following the second time period, determining a responsiveness of the subject to the second therapeutically effective amount, to thereby determine if the subject is not fully responsive (as described herein) to the second therapeutically effective amount. If the subject is determined as not fully responsive, the method or treatment further comprises administering to the subject, during a third time period, a third therapeutically effective amount, which is higher than the second therapeutically effective amount.

In some embodiments, the stages of determining responsiveness and, if appropriate, increasing an amount of buprenorphine to be administered, are repeated further.

Thus, the method or treatment may optionally comprise administering a fourth therapeutically effective amount during a fourth time period, optionally also a fifth therapeutically effective amount during a fifth time period, optionally also a sixth therapeutically effective amount during a sixth time period, and so forth.

Herein, a reference to a therapeutically effective amount in the context of any of the aspects of the invention, which does not include a reference to a "first" amount, "second" amount, "third" amount, or the like, is to be understood as referring to a "therapeutically effective amount" as described herein in general and/or to a "first therapeutically effective amount" as described herein.

In some embodiments, the first therapeutically effective amount is about 0.2 mg/day or less. In some embodiments, the first therapeutically effective amount is less than 0.2 mg/day. In such embodiments, any daily dosage described herein which is higher than a range described for the first therapeutically effective amount (e.g., 0.2 mg per day or more) is applicable only to a higher therapeutically effective amount, for example, a second therapeutically effective amount, a third therapeutically effective amount, and so forth.

In some embodiments, the first therapeutically effective amount is 0.18 mg per day or less. In some embodiments, the first therapeutically effective amount is 0.16 mg per day or less. In some embodiments, the first therapeutically effective amount is 0.15 mg per day or less. In some embodiments, the first therapeutically effective amount is 0.14 mg per day or less. In some embodiments, the first therapeutically effective amount is 0.13 mg per day or less. In some embodiments, the first therapeutically effective amount is 0.12 mg per day or less. In some embodiments, the first therapeutically effective amount is 0.11 mg per day or less.

In some embodiments, the first therapeutically effective amount is zero (e.g., a placebo).

In some embodiments, the first therapeutically effective amount is more than zero. In some embodiments, the first therapeutically effective amount is at least 0.01 mg per day. In some embodiments, the first therapeutically effective amount is at least 0.02 mg per day. In some embodiments, the first therapeutically effective amount is at least 0.03 mg per day. In some embodiments, the first therapeutically effective amount is at least 0.04 mg per day. In some embodiments, the first therapeutically effective amount is at least 0.05 mg per day. In some embodiments, the first therapeutically effective amount is at least 0.06 mg per day. In some embodiments, the first therapeutically effective amount is at least 0.07 mg per day. In some embodiments, the first therapeutically effective amount is at least 0.08 mg per day. In some embodiments, the first therapeutically effective amount is at least 0.09 mg per day. In some embodiments, a second therapeutically effective amount is at least 0.1 mg per day. In some embodiments, a second therapeutically effective amount is at least 0.11 mg per day. In some embodiments, a second therapeutically effective amount is at least 0.12 mg per day. In some embodiments, a second therapeutically effective amount is at least 0.13 mg per day. In some embodiments, a second therapeutically effective amount is at least 0.14 mg per day. In some embodiments, a second therapeutically effective amount is at least 0.15 mg per day. In some embodiments, a second therapeutically effective amount is at least 0.16 mg per day.

In some embodiments, a first therapeutically effective amount is in a range of from 0.01 to 0.18 mg per day. In some embodiments, a first therapeutically effective amount is in a range of from 0.02 to 0.15 mg per day. In some embodiments, a first therapeutically effective amount is in a range of from 0.03 to 0.13 mg per day. In some embodiments, a first therapeutically effective amount is in a range of from 0.04 to 0.11 mg per day. In exemplary embodiments, a first therapeutically effect amount is in a range of from about 0.05 mg per day to about 0.15 mg per day. In further exemplary embodiments, a first therapeutically effect amount is in a range of from about 0.05 mg per day to about 0.12 mg per day. In further exemplary embodiments, a first therapeutically effect amount is in a range of from about 0.08 mg per day to about 0.15 mg per day. In further exemplary embodiments, a first therapeutically effect amount is in a range of from about 0.08 mg per day to about 0.12 mg per day. In further exemplary embodiments, a first therapeutically effect amount is in a range of from about 0.07 mg per day and about 0.15 mg per day. In further exemplary embodiments, a first therapeutically effect amount is in a range of from about 0.07 mg per day and about 0.12 mg per day. In further exemplary embodiments, a first therapeutically effect amount is in a range of from about 0.05 mg per day to about 0.12 mg per day. In further exemplary embodiments, a first therapeutically effect amount is in a range of from about 0.05 mg per day to about 0.1 mg per day. Any intermediate amount within these values in contemplated.

In some embodiments, a second therapeutically effective amount is at least 0.1 mg per day. In some embodiments, a second therapeutically effective amount is at least 0.2 mg per day. In exemplary embodiments, a second therapeutically effect amount is in a range of from about 0.1 mg per day to about 0.2 mg per day. In some embodiments, a second therapeutically effective amount is in a range of from 0.1 to 0.3 mg/day. In some embodiments, a second therapeutically effective amount is in a range of from 0.12 to 0.28 mg/day. In some embodiments, a second therapeutically effective amount is in a range of from 0.14 to 0.26 mg/day. In some embodiments, a second therapeutically effective amount is in a range of from 0.16 to 0.24 mg/day. In some embodiments, a second therapeutically effective amount is in a range of from 0.18 to 0.22 mg/day. In further exemplary embodiments, a second therapeutically effective amount is about 0.2 mg/day. Any intermediate amount within these values in contemplated.

In some embodiments, a third therapeutically effective amount is at least 0.2 mg per day. In some embodiments, a third therapeutically effective amount is at least 0.3 mg per day. In some embodiments, a third therapeutically effective amount is at least 0.4 mg per day. In exemplary embodiments, a third therapeutically effect amount is in a range of from about 0.2 mg per day to about 0.4 mg per day. In some embodiments, a third therapeutically effect amount is in a range of from 0.2 mg per day to 0.5 mg per day. In some embodiments, a third therapeutically effect amount is in a range of from 0.3 mg per day to 0.5 mg per day. In some embodiments, a third therapeutically effect amount is in a range of from 0.32 mg per day to 0.48 mg per day. In some embodiments, a third therapeutically effect amount is in a range of from 0.34 mg per day to 0.46 mg per day. In some embodiments, a third therapeutically effect amount is in a range of from 0.36 mg per day to 0.44 mg per day. In some embodiments, a third therapeutically effect amount is in a range of from 0.38 mg per day to 0.42 mg per day. In further exemplary embodiments, a third therapeutically effect amount is about 0.4 mg per day. Any intermediate amount within these values in contemplated.

As exemplified herein, beginning buprenorphine administration with a relatively low daily dosage (e.g., less than 0.2 mg per day, as compared with a higher dosage of 0.2-1.6 mg per day) was found to be associated with low levels of adverse side effects, as well as with better compliance of patients with the treatment, as evidenced by a lower dropout rate.

Without being bound by any particular theory, it is believed that administering a first therapeutically effective amount which is relatively low, and then increasing the dosage (e.g., to a second therapeutically effective amount, and optionally further to a third therapeutically effective amount), allows for better avoidance of adverse side effects by facilitating gradual adaptation of the subject to the buprenorphine and/or by facilitating identification of potentially harmful side effects at low dosages, rather than at higher dosages when the side effects would be more harmful.

As further exemplified herein, daily dosages of 0.1 mg/day buprenorphine have a significant therapeutic effect, and beginning buprenorphine administration with such a relatively low daily dosage does not adversely affect outcome.

Without being bound by any particular theory, it is therefore believed that for any given subject, there will be a significant chance that the subject will be fully responsive to the relatively low first therapeutically effective dose, whereas there will be little danger that a relatively low first therapeutically effective amount will adversely affect outcome. It is further believed that a strong placebo effect in the first several days of treatments renders the specific daily dosage of buprenorphine used during that time period relatively non-critical (e.g., the placebo effect may outweigh an effect of any daily dosage of buprenorphine), such that there is little or no downside to administering a low dosage during that time period (e.g., in order to minimize side effects).

In some embodiments, increasing a dosage (e.g., replacing a first therapeutically effective amount with a second therapeutically effective amount, replacing a second therapeutically effective amount with a third therapeutically effective amount, and so forth) comprises increasing a dosage by an amount which is about 10%, about 20%, about 25%, about 33%, and/or about 50% of the final dosage.

In some embodiments, increasing a dosage comprises increasing a dosage by increments of about 0.02 mg, about 0.03 mg, about 0.04 mg, about 0.05 mg, about 0.1 mg, about 0.2 mg, about 0.3 mg, about 0.4 mg, about 0.5 mg and/or about 1 mg.

In some embodiments, increasing a dosage is performed in one step, e.g., simply replacing a first therapeutically effective amount with a second therapeutically effective amount, simply replacing a second therapeutically effective amount with a third therapeutically effective amount.

In alternative embodiments, a dosage is increased gradually, i.e., the dosage is increased more than once (i.e., at least one intermediate dosage is administered) until the intended dosage is reached. For example, administering a second therapeutically effective amount instead of a first therapeutically effective amount may comprise administering one or more intermediate dosages which are between the first and second therapeutically effective amounts.

In some embodiments, at least one intermediate dosage is administered (e.g., one intermediate dosage is administered for one day while the dosage is being increased). In some embodiments, at least two intermediate dosages are administered (e.g., two intermediate dosage are administered, one for each of two days while the dosage is being increased). In some embodiments, at least three intermediate dosages are administered (e.g., three intermediate dosage are administered, one for each of three days while the dosage is being increased.

When a dosage is increased more than once (e.g., when first, second and third therapeutically effective amounts are administered, as described herein), the various increases in dosage may be the same (e.g., a dosage may be increased by increments of 0.1 mg) or different (e.g., a dosage may be increased by 0.1 mg, and later by 0.2 mg).

In some embodiments, a time period during which a particular therapeutically effective amount of buprenorphine is administered, as described herein (e.g., a first time period, a second time period, a third time period, and so forth) is at least 3 days, optionally in a range of from 3 days to 3 weeks. In some embodiments, the time period is at least 4 days, optionally in a range of from 4 days to 3 weeks. In some embodiments, the time period is at least 5 days, optionally in a range of from 5 days to 3 weeks. In some embodiments, the time period is at least 6 days, optionally in a range of from 6 days to 3 weeks. In some embodiments, the time period is at least 7 days (one week), optionally in a range of from 7 days to 3 weeks. In some embodiments, the time period is at least 8 days, optionally in a range of from 8 days to 3 weeks. In some embodiments, the time period is at least 9 days, optionally in a range of from 9 days to 3 weeks. In some embodiments, the time period is at least 10 days, optionally in a range of from 10 days to 3 weeks.

In some embodiments, a maximum duration cannot be predetermined for a time period, as the length of a time period will depend whether the subject is determined as fully responsive to the administered buprenorphine dosage. For example, if after one week a subject is determined to be fully responsive to an administered dosage of buprenorphine, but after two weeks the subject is determined to be not fully responsive, such that the time period for administration of that dosage is approximately two weeks, it is to be appreciated that the duration of the time period could not be predicted beforehand or predetermined.

In some embodiments, a minimum duration for a time period is predetermined by scheduling the determining of responsiveness as described herein. For example, if evaluation of the subject is scheduled to be after 7 days of administering a given therapeutically effective amount, then the time period for that amount will be at least 7 days (and possibly longer, as described hereinabove).

According to some embodiments, administration is effected by a route selected from the group consisting of sublingual administration, transdermal administration, intravenous injection and/or infusion, intramuscular injection and/or infusion, and intranasal administration.

Pharmaceutical Composition and Unit Dosage Form:

In any of the methods, treatments and uses described herein, the buprenorphine can be utilized either per se, or preferably, as a part of a pharmaceutical composition which further comprises a pharmaceutically acceptable carrier, as defined herein.

According to another aspect of embodiments of the invention, there is provided a pharmaceutical composition comprising buprenorphine and a pharmaceutically acceptable carrier. In some embodiments, the pharmaceutical composition is packaged in a packaging material and identified in print, in or on the packaging material, for use in the treatment of acute suicidality (e.g., a treatment as described herein). In some embodiments, the pharmaceutical composition is otherwise identified for use in the treatment of acute suicidality.

As used herein, a "pharmaceutical composition" refers to a preparation of an active compound (e.g., buprenorphine), with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In some embodiments, the pharmaceutical composition is identified for administration once per day (e.g., as described herein).

In some embodiments, the pharmaceutical composition comprises a unit dosage form, comprising a therapeutically effective amount of buprenorphine.

The term "unit dosage form", as used herein, describes physically discrete units, each unit containing a predetermined quantity of buprenorphine calculated to produce the desired therapeutic effect, in association with at least one pharmaceutically acceptable carrier, diluent, excipient, or combination thereof.

The amount of buprenorphine in the unit dosage form may optionally be a daily dosage of buprenorphine, as described herein (e.g., in a range of from 0.02 to 0.5 mg), such that a method or treatment such as described herein may be effected by administration of one unit dosage form per day.

Alternatively, the amount of buprenorphine in the unit dosage form may be, for example, half a daily dosage described herein, such that a method or treatment described herein may be effected by administration of two unit dosage forms per day; or a third or a quarter of a daily dosage described herein, such that a method or treatment described herein may be effected by administration of three or four unit dosage forms per day, respectively.

In some embodiments, the amount of buprenorphine in the unit dosage form is a daily dosage of buprenorphine corresponding to a first therapeutically effective amount, as described herein (e.g., less than 0.2 mg), such that administration of a first therapeutically effective amount such as described herein may be effected by administration of one unit dosage form per day.

In some embodiments, administration of a second therapeutically effective amount is effected by administration of two or more (optionally two) unit dosage forms per day.

In some embodiments, administration of a third therapeutically effective amount is effected by administration of two or more (optionally 2, optionally 3, and optionally 4) unit dosage forms per day.

In some embodiments, the unit dosage form comprises less than 0.2 mg buprenorphine. In some embodiments the unit dosage form comprises from 0.05 to 0.1 mg buprenorphine. In some embodiments administration of a first therapeutically effective amount is effected by administration of one such unit dosage form per day. In some embodiments administration of a higher therapeutically effective amount (e.g., a second or third therapeutically effective amount) is effected by administration of two such unit dosage forms per day, in some embodiments three unit dosage forms per day, and in some embodiments, four such unit dosage forms per day.

In some embodiments the unit dosage form comprises about 0.1 mg buprenorphine. In some embodiments administration of a first therapeutically effective amount or a second therapeutically effective amount is effected by administration of one such unit dosage form per day. In some embodiments administration of about 0.2 mg/day (e.g., as a second or third therapeutically effective amount) is effected by administration of two such unit dosage forms per day, and in some embodiments, administration of about 0.4 mg/day (e.g., as a third or fourth therapeutically effective amount) is effected by administering four such unit dosage forms per day.

In some embodiments the unit dosage form comprises from 0.01 to 0.18 mg buprenorphine. In some embodiments, the unit dosage form comprises from 0.02 to 0.15 mg. In some embodiments the unit dosage form comprises from 0.03 to 0.13 mg. In some embodiments the unit dosage form comprises from 0.04 to 0.11. In some embodiments the unit dosage form comprises from about 0.05 to about 0.15 mg. In some embodiments the unit dosage form comprises from about 0.05 mg to about 0.12 mg. In some embodiments the unit dosage form comprises from about 0.08 mg to about 0.15 mg. In some embodiments the unit dosage form comprises from about 0.08 mg to about 0.12 mg. In some embodiments the unit dosage form comprises from about 0.07 mg to about 0.15 mg. In some embodiments the unit dosage form comprises from about 0.07 mg to about 0.12 mg. In some embodiments the unit dosage form comprises from about 0.05 mg to about 0.12 mg. In some embodiments the unit dosage form comprises from about 0.05 mg to about 0.1 mg. Any intermediate amount within these values in contemplated.

In some embodiments the unit dosage form comprises about 0.05 mg buprenorphine. In some embodiments administration of a first therapeutically effective amount is effected by administration of one such unit dosage form per day. In some embodiments administration of about 0.1 mg/day (e.g., as a first or second therapeutically effective amount) is effected by administration of two such unit dosage forms per day, and in some embodiments, administration of about 0.2 mg/day (e.g., as a second or third therapeutically effective amount) is effected by administering four such unit dosage forms per day.

In some embodiments the unit dosage form comprises about 0.2 mg buprenorphine. In some embodiments administration of a second or third therapeutically effective amount is effected by administration of one such unit dosage form per day. In some embodiments administration of about 0.4 mg/day (e.g., as a third or fourth therapeutically effective amount) is effected by administration of two such unit dosage forms per day.

In some embodiments the unit dosage form comprises about 0.4 mg buprenorphine. In some embodiments administration of a third or fourth therapeutically effective amount is effected by administration of one such unit dosage form per day.

In some embodiments, two or more of the unit dosage forms described herein are used in combination to achieve a desired dosage, for example, combining a unit dosage form comprising about 0.05 mg with one comprising about 0.1 mg so as to administer 0.15 mg, combining a unit dosage form comprising about 0.1 mg with one comprising about 0.2 mg so as to administer 0.3 mg, and the like.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the buprenorphine into preparations which can be used pharmaceutically. Proper formulation is dependent upon the route of administration chosen.

For transdermal administration, the pharmaceutical composition may optionally be present in a patch, a swab, a pledget, and/or a pad.

Transdermal patches and the like may comprise some or all of the following components: a pharmaceutical composition (e.g., as described herein), a liner for protecting the patch during storage, which is optionally removed prior to use, an adhesive for adhering different components together and/or adhering the patch to the skin, a backing which protects the patch from the outer environment, and/or a membrane which controls release of a drug into the skin.

Methods and treatments described herein may optionally be effected using commercially available transdermal buprenorphine administration systems (such as transdermal patches), including, for example, Transtec® (Grunenthal) or Butrans® (Purdue Pharma) patches.

For sublingual, buccal and oral administration, the buprenorphine can be formulated readily by combining the buprenorphine with pharmaceutically acceptable carriers well known in the art. Such carriers enable the buprenorphine to be formulated as tablets, lozenges, pills, dragees, capsules, sublingual films, liquids (e.g., an ethanol-based solution), gels, syrups, slurries, suspensions, and the like, for oral ingestion by a patient.

For sublingual and buccal administration, the compositions optionally take the form of tablets or lozenges formulated in a conventional manner. For sublingual administration, the compositions may optionally take the form of a sublingual film (e.g., a quickly dissolving film formulated similarly to a quickly dissolving tablet, but in the shape of a film which fits under the tongue).

Methods and treatments described herein may optionally be effected using commercially available buprenorphine tablets for sublingual administration, including, for example, Subutex® and Suboxone® tablets or sublingual films (Reckitt Benckiser).

Pharmacological preparations for sublingual, buccal or oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of doses of buprenorphine.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the buprenorphine may be dissolved or suspended in suitable liquids. In addition, stabilizers may be added.

All formulations for sublingual, buccal and oral administration should be in dosages suitable for the chosen route of administration.

For transmucosal administration, penetrants are optionally used in the formulation. Such penetrants are generally known in the art.

For administration by inhalation (e.g., intranasal administration), the buprenorphine is conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of buprenorphine and a suitable powder base such as, but not limited to, lactose or starch.

For injection or infusion, the buprenorphine may be formulated in aqueous solutions, preferably in physiologically compatible buffers such as Hank's solution, Ringer's solution, or physiological saline buffer with or without organic solvents such as propylene glycol, polyethylene glycol.

Injection and/or infusion of buprenorphine may be by intravenous, intramuscular and/or subcutaneous routes.

The buprenorphine may be formulated for parenteral administration, e.g., by bolus injection or continuous infusion. Formulations for injection or infusion may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of buprenorphine in water-soluble form. Additionally, suspensions of buprenorphine may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the buprenorphine to allow for the preparation of highly concentrated solutions. Alternatively, the buprenorphine may be in powder form for constitution with a suitable vehicle, e.g., sterile, pyrogen-free water, before use.

Methods and treatments described herein may optionally be effected using commercially available buprenorphine solutions for parenteral administration (e.g., intramuscular or intravenous administration), including, for example, Temgesic® and Buprenex® injections (Reckitt Benckiser).

The buprenorphine may optionally be formulated for subcutaneous or intramuscular injection of a liquid polymer matrix for sustained release of buprenorphine. The sustained release may be formulated for sustained release of buprenorphine over a time period of, for example, 3 days, 4 days, 5 days, 6 days, 7 days, two weeks, three weeks, four weeks, two months, three months, and even 6 months.

Methods and treatments described herein may optionally be effected using commercially available sustained release formulations for subcutaneous injection, such as, for example, Probuphine® formulations.

The buprenorphine may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing buprenorphine. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising buprenorphine formulated in a compatible pharmaceutical carrier may also be prepared, placed in an appropriate container, and labeled for treatment of acute suicidality, as is detailed herein.

Buprenorphine-containing compositions which are not intended for intravenous injection may further comprise and ingredient designed for discouraging abuse of the composition by intravenous injection. For example, an opioid antagonist such as naloxone may be included, wherein the opioid antagonist is not absorbed when the composition is administered as intended, but negates the effect of buprenorphine if the composition is injected intravenously.

According to another aspect of embodiments of the invention, there is provided a pharmaceutical composition unit dosage form comprising buprenorphine, or a pharmaceutically acceptable salt thereof, in an amount of less than 0.2 mg buprenorphine (e.g., any amount of less than 0.2 mg, as described herein).

In some embodiments the unit dosage form comprises from 0.01 to 0.18 mg buprenorphine. In some embodiments, the unit dosage form comprises from 0.02 to 0.15 mg. In some embodiments the unit dosage form comprises from 0.03 to 0.13 mg. In some embodiments the unit dosage form comprises from 0.04 to 0.11. In some embodiments the unit dosage form comprises from about 0.05 to about 0.15 mg. In some embodiments the unit dosage form comprises from about 0.05 mg to about 0.12 mg. In some embodiments the unit dosage form comprises from about 0.08 mg to about 0.15 mg. In some embodiments the unit dosage form comprises from about 0.08 mg to about 0.12 mg. In some embodiments the unit dosage form comprises from about 0.07 mg to about 0.15 mg. In some embodiments the unit dosage form comprises from about 0.07 mg to about 0.12 mg. In some embodiments the unit dosage form comprises from about 0.05 mg to about 0.12 mg. In some embodiments the unit dosage form comprises from about 0.05 mg to about 0.1 mg. Any intermediate amount within these values in contemplated.

In some embodiments, the unit dosage form is for use in the treatment of acute suicidality in a subject in need thereof (e.g., as described herein). In some embodiments, the unit dosage form is packaged in a packaging material and identified for use, in or on the packaging material, for use in the treatment of acute suicidality in a subject in need thereof.

In some embodiments, the unit dosage forms are for a treatment wherein increasing a therapeutically effective amount as described herein (e.g., from a first therapeutically effective amount to a second therapeutically effective amount and/or from a second therapeutically effective amount to a third therapeutically effective amount, and so forth) is effected by increasing a number of unit dosage forms (as described herein) which are administered per day.

In some embodiments, the treatment of acute suicidality comprises administration of one unit dosage form (as described herein) per day as a therapeutically effective amount as described herein (e.g., a first therapeutically effective amount).

In some embodiments, the treatment of acute suicidality comprises administration of two unit dosage forms (as described herein) per day as a second therapeutically effective amount as described herein.

In some embodiments, the treatment of acute suicidality comprises administration of three or more unit dosage forms (as described herein) per day as a third therapeutically effective amount as described herein. In some embodiments, the third therapeutically effective amount is effected by administration of four unit dosage forms (as described herein) per day.

In some embodiments, the unit dosage form is for use in the treatment any other condition in which administration of buprenorphine may be effective. In some embodiments, the unit dosage form is packaged in a packaging material and identified for use, in or on the packaging material, for use in the treatment of a condition in which administration of buprenorphine may be effective.

It is expected that during the life of a patent maturing from this application relevant conditions will be found to be treatable by buprenorphine treatment according to a regimen and/or unit dosage form described herein, and the scope of the phrase "condition in which administration of buprenorphine may be effective" in this application is intended to include all such new conditions a priori.

It is expected that during the life of a patent maturing from this application many relevant revised versions of the tests described herein (e.g., Beck Suicidal Ideation (BSI) scale, Suicide Probability Scale (SPS), Columbia-Suicide Severity Rating Scale (C-SSRS), Overt Aggression Scale Modified (OAS-M), Holden Psychache Scale (PAS), and Orbach and Mikulincer Mental Pain (OMMP) scale) will be developed and the scope of terms describing such tests (e.g., the aforementioned tests) is intended to include all such new techniques a priori.

It is expected that during the life of a patent maturing from this application relevant revised versions of the American Psychiatric Association's Diagnostic and Statistical Manual of Mental Disorders (DSM) will be developed and published (e.g., DSM-V) and the scope of definitions of mental disorders mentioned in this application (e.g., the aforementioned diagnostic definitions) is intended to include all such new versions a priori.

Herein throughout, the phrases "in some embodiments", "in some embodiments of any of the aspects of the invention described herein" and "in some of the embodiments of any of the aspects of the invention described herein" are used interchangeably and are meant to encompass any combination to the embodiments described following these phrases and any other embodiments which are described in the instant application for any of the described aspects.

For a non-limiting example, some embodiments of the present invention that relate to "acute suicidality" are disclosed in the context of any of the embodiments of the methods and treatments as described herein.

As used herein the term "about" refers to ±25%. According to optional embodiments, the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:
Buprenorphine (hydrochloride) sublingual tablets (0.2 mg buprenorphine) were obtained from C.T.S. Chemical Industries Ltd. (Kiryat Malachi, Israel).
Clinical Symptom Evaluation:
Suicidality is evaluated using the following methods:
Beck Suicidal Ideation (BSI) scale [Beck & Steer, *Manual for the Beck Scale for Suicide Ideation*. San Antonio, Tex.: Psychological Corporation (1991)];
Suicide Probability Scale (SPS) [Cull & Gill, *Suicide Probability Scale Manual*. Los Angeles, Calif. (1988)];
Columbia-Suicide Severity Rating Scale (C-SSRS) [Posner et al., *CNS Spectr*, 12:156-162 (2007)]; and Overt Aggression Scale Modified (OAS-M) [Coccaro et al., *J Neuropsychiatry Clin Neurosci*, 3:S44-51 (1991)].
Psychache is evaluated using the following methods:
Holden Psychache Scale (PAS) [Holden et al., *Canadian J Behav Sci*, 33:224-232 (2001)]; and
Orbach and Mikulincer Mental Pain (OMMP) scale [Orbach et al., *Suicide Life Threat Behav*, 33:231-241 (2003)].

In addition, levels of depression are evaluated using a Beck Depression Inventory, second version (BDI-II) [Beck et al., *J Pers Assess*, 67:588-597 (1996)]; hopelessness is evaluated using a Beck Hopelessness Scale (BHS) [Beck & Steer, *Manual for the Beck Hopelessness Scale*. San Antonio, Tex.: Psychological Corporation (1988)]; general clinical impressions are evaluated using a Clinical Global Impressions (CGI) scale [Guy et al., *Clinical Global Impressions*. In: *ECDEU Assessment Manual for Psychopharmacology*. National Institute of Mental Health: Rockville. 218-222 (1976)]; attachment is assessed as described by Mikulincer & Erev [*Br J Soc Psychol*, 30:273-291 (1991)] and Mikulincer et al. [*J Pers Soc Psychol*, 58:273-280 (1990)]; and environmental and psychosocial factors contributing to disorders are determined according to Axis IV of the DSM-IV.

Statistics:
Data were analyzed using suitable software (e.g., SPSS software (version 14)). Demographic data were analyzed using a Fisher's Exact Test or a t-test. Determination of differences in symptoms between buprenorphine-treated and placebo-treated patients was determined using t-tests and/or $\chi^2$ tests, as appropriate, or multivariate analysis of variance (ANOVA) with repeated measures. Correlations between continuous variables were analyzed by Pearson and/or Spearman correlations, as appropriate. Statistical significance was determined as $P<0.05$.

Example 1

Effect of Buprenorphine Treatment on Acute Suicidality (Pilot Study)

A placebo-controlled double-blind study was designed in order to evaluate the effect of buprenorphine on acute suicidality.

Patients suffering from suicidal ideation or behavior were recruited from the Abarbanel Mental Health Center (Bat-Yam, Israel), and from the emergency room of the Edith Wolfson Medical Center (Holon, Israel). Patients included men and women, ages 18-60, who exhibited suicidal ideation or behavior, characterized by a score of more than 6 on the Beck Suicidal Ideation scale.

Exclusion criteria were as follows:
electroconvulsive therapy (ECT) within the last month;
schizophrenia;
current psychosis;
substance abuse or alcohol abuse within the last two years;
benzodiazepine dependence within the last 6 months;
any significant systemic illness or unstable medical condition which does not permit inclusion, according to the research physician;
pregnant and nursing women; and
patients who currently suffer from severe impairment or dysfunction of liver, kidney, adrenal gland, gall, closed brain injury, urinary retention or respiratory system.

Patients were randomly assigned buprenorphine treatment (7 patients) or placebo treatment (8 patients). Buprenorphine and placebos were administered for two weeks. Patients in the buprenorphine group received 0.2-1.6 mg buprenorphine per day, with the starting dose being 0.2 mg per day, followed by a gradual increase up to the maximal dose during the first week.

3 patients receiving buprenorphine did not complete the treatment due to nausea. 2 patients were not included in the final analysis, one because of poor compliance with the treatment, and one who claimed to provide false information in order to be released from the hospital. The final analysis included 6 patients receiving placebo and 4 patients receiving buprenorphine.

Treatment with additional medications was determined according to the judgment of the physician, independently of the buprenorphine/placebo.

All patients were evaluated by the Structured Clinical Interview for DSM-IV, Axis I and II (SCID) [First et al., Biometrics Research Department, New York State Psychiatric Institute, New York (1995); First et al., American Psychiatric Press, Washington, D.C. (1997)]. Patients also filled up a demographic questionnaire which includes basic demographic information such as age, gender, education, income, etc., as well as information regarding clinical history.

Each patient was interviewed 3 times, at weekly intervals, and the results were evaluated to determine clinical symptoms. Suicidality was evaluated according to a Beck Suicidal Ideation (BSI) scale, psychache was evaluated according to a Holden Psychache scale (PAS), and depression was evaluated according to a Beck Depression Inventory (BDI-II).

The BSI scale is a scale of 0-38 (high score indicates a high degree of suicidality), based on 19 items in a questionnaire, wherein each item may be scored as 0, 1 or 2. The BSI questionnaire includes items for evaluating the active will to commit suicide ("active aspect"), will to not be alive ("passive aspect"), and potential lethality and the degree of concreteness of specific plans to commit suicide ("specific aspect"). These aspects were also scored separately.

The PAS is a scale of 13-65 (high score indicates a high degree of psychache), based on 13 items in a questionnaire, wherein each item may be scored on a scale of 1-5.

The BDI scale is a scale of 0-63 (scores of 14-19 indicate mild depression, 20-28 indicates moderate depression, and 29 or more indicates severe depression), based on 21 items in a questionnaire, wherein each item is scored on a scale of 0-3. The BDI questionnaire includes items for evaluating the severity of depressed feelings ("affective aspect"), physical signs and symptoms associated with depression ("somatic aspect") and depressive thoughts ("cognitive aspect") [Buckley et al., *J Subst Abuse Treat*, 20:197-204 (2001)]. These three aspects were also scored separately.

In addition, patients were examined 3 times, at weekly intervals, to confirm that no significant adverse side effects or worsening of mental health occurred.

There was no statistically significant difference between the buprenorphine and placebo groups with respect to DSM-IV diagnosis, suicidality (BSI scores) prior to treatment, depression (BDI-II scores) prior to treatment, age, years of education, time of most recent hospitalization, number of previous hospitalizations, number of suicide attempts, or family status. However, after the blinds were opened, it was found that the buprenorphine group included significantly ($P<0.05$) more males than did the placebo group (4/4 vs. 1/6). In addition, the placebo group exhibited higher levels of depression prior to treatment than did the buprenorphine group, to a degree which was close to significant ($p=0.053$).

The mean scores for suicidality (BSI), depression (BDI-II) and psychache (PAS) are summarized in Table 1.

TABLE 1

Mean scores (±standard deviation) for suicidality, depression and psychache in patients treated with buprenorphine or placebo

| | Scale | Treatment | Baseline | Week 1 | Week 2 |
|---|---|---|---|---|---|
| Suicidality score (Beck Suicidality Ideation scale) | Total score | Buprenorphine | 17 ± 3.1 | 10.2 ± 3.7 | 9 ± 1.4 |
| | | Placebo | 19 ± 15.2 | 10.3 ± 5.7 | 14 ± 8.7 |
| | Passive aspect | Buprenorphine | 2.7 ± 0.5 | 1.5 ± 1 | 1.7 ± 0.9 |
| | | Placebo | 3.6 ± 1 | 2.1 ± 1.9 | 3.1 ± 1.8 |
| | Active aspect | Buprenorphine | 11 ± 4.1 | 7 ± 3.5 | 6.5 ± 1.7 |
| | | Placebo | 11 ± 2.8 | 6 ± 3 | 8.1 ± 7 |
| | Specific aspect | Buprenorphine | 1.7 ± 1.7 | 0.7 ± 0.9 | 0.5 ± 0.5 |
| | | Placebo | 2.6 ± 1.9 | 1 ± 1.6 | 1.6 ± 1.5 |
| Depression score (Beck Depression Inventory) | Total score | Buprenorphine | 31.5 ± 3.8 | 20 ± 7.7 | 15.5 ± 12.8 |
| | | Placebo | 42 ± 8.5 | 29.6 ± 11.2 | 35.7 ± 5.6 |
| | Affective aspect | Buprenorphine | 7.5 ± 1.7 | 4 ± 1.5 | 2.5 ± 1.2 |
| | | Placebo | 8.3 ± 1.4 | 6.5 ± 1.2 | 8.5 ± 1 |
| | Somatic aspect | Buprenorphine | 12 ± 1.4 | 8.5 ± 2.6 | 5 ± 2.1 |
| | | Placebo | 16.5 ± 1.1 | 12 ± 2.1 | 13 ± 1.7 |
| | Cognitive aspect | Buprenorphine | 11.7 ± 1.5 | 6.7 ± 1.6 | 7.2 ± 2.2 |
| | | Placebo | 17.1 ± 1.2 | 10.6 ± 1.3 | 14.1 ± 1.8 |
| Psychache score | | Buprenorphine | 49 ± 8.8 | 37.5 ± 6.2 | 33.2 ± 8.9 |
| | | Placebo | 56.6 ± 3.5 | 39.5 ± 3.5 | 43 ± 9.2 |

As shown in FIG. 1 and in Table 1, the suicidality of patients treated with buprenorphine for two weeks decreased considerably more than in patients treated with placebo.

These results suggest that buprenorphine is effective at reducing acute suicidality.

As shown in Table 1, the degree of depression of patients treated with buprenorphine for two weeks decreased more than in patients treated with placebo.

Overall, there was no significant correlation between the decrease in suicidality and the decrease in depression in individuals ($r=0.387$; $p=0.1$). Notably, there was a significant correlation between the decrease in suicidality and the decrease in depression in individuals of the placebo group ($r=0.871$; $p=0.024$), but there was no such correlation in individuals of the buprenorphine group ($r=0.674$; $p=0.326$).

These results suggest that the effect of buprenorphine on suicidality is not dependent on the effect of buprenorphine on depression.

Example 2

Phase III Clinical Study of the Effect of Buprenorphine Treatment on Acute Suicidality A phase III placebo-controlled double-blind study was designed in order to confirm the efficacy of buprenorphine for reducing acute suicidality, and in order to evaluate the ability of buprenorphine to reduce suicidality by mechanisms other than reduction of depression (e.g., in non-depressed patients).

In order to facilitate statistical analysis of the results and to obtain a higher degree of statistical certainty than in the study described in Example 1, a larger group of patients was studied. For similar reasons, treatment was for a longer period of time (4 weeks) than in the study described in Example 1 (2 weeks).

Patients suffering from suicidal ideation or behavior were recruited from the Abarbanel Mental Health Center (Bat-Yam, Israel) and affiliated mental health clinics, from the emergency room of the Edith Wolfson Medical Center (Holon, Israel), or from The Ramat Chen Mental Health Clinic (Ramat Gan, Israel). Patients included men and women, ages 18-65, who exhibited suicidal ideation or behavior, characterized by a score of at least 6 on the Beck Suicidal Ideation scale.

Exclusion criteria were as follows:
electroconvulsive therapy (ECT) within the last month;
psychotic features within the last 3 months;
history of schizophrenia, substance abuse or alcohol abuse within the last two years;
benzodiazepine dependence within the last two years;
any significant systemic illness or unstable medical condition which does not permit inclusion, according to the research physician;
pregnant women; and
patients who currently suffer from severe impairment or dysfunction of liver, kidney, adrenal gland, gall, closed brain injury, urinary retention or respiratory system.

91 patients were recruited into the study and randomly assigned to receive either buprenorphine or placebo in a 2:1 ratio (buprenorphine:placebo). 16 patients dropped out of the study before completing 3 assessments. 13 patients discontinued the study due to side effects. 9 patients were not included in the final data analysis because of a total baseline BSI score of less than 11, or an answer of "0" to items 4 and 5 of the BSI at baseline. 5 patients were not included in the final data analysis because of documented noncompliance with the study medication. 5 patients were not included in the final data analysis because of documented unreliability in their answers to the study questionnaires. 1 patient was not included due to psychosis. 1 patient was not included due to taking narcotic analgesics during the study. 1 patient became pregnant during the study and her participation was discontinued. 1 patient discontinued the study at the request of his treating physician. 39 patients (25 who received buprenorphine and 14 who received placebo) completed at least 3 assessments, and were included in the final data analysis.

All but 3 patients received a dose of 0.1-0.8 mg (buprenorphine or placebo) per day, with the most frequently used starting dose being 0.1 mg per day. The starting dose was gradually titrated upwards to a maximal dose of 0.8 mg/day or less by the end of the study period (except for the 3 subjects mentioned above, of whom 1 received buprenorphine and 2 received placebo, at a final dose of 1.6 mg/day). However, slower titration was performed in response to either side effects or remission of suicidal symptoms, such that most patients in the current study received a maximal dose of 0.4 mg/day (buprenorphine or placebo) by the end of the study period. Of the 25 patients who received buprenorphine, 12 received a maximal dose of 0.2 mg/day, another 8 patients received a maximal dose of 0.4 mg/day, 2 received a maximal dose of 0.6 mg/day, 2 received a maximal dose of 0.8 mg/day, and 1 received a maximal dose of 1.6 mg/day.

Treatment with additional medications was determined according to the judgment of the treating physician, independently of the buprenorphine/placebo.

All patients were evaluated by the Structured Clinical Interview for DSM-IV, Axis I and II, and filled out a questionnaire for basic demographic information and clinical history (as described in Example 1).

Each patient was interviewed 5 times, at weekly intervals, and the results were evaluated to determine clinical symptoms. Suicidality, psychache, depression and other symptoms were evaluated using the methods described in the Materials and Methods section hereinabove.

In addition, patients were examined 6 times, at weekly intervals, during the duration of medication administration, and one week following discontinuation of the study medication, to confirm that no significant adverse side effects, withdrawal symptoms, or worsening of mental health occurred. None of the patients suffered from withdrawal symptoms.

Results were analyzed primarily in order to quantify a reduction in suicidality after 4 weeks of buprenorphine treatment (as compared to placebo), as expressed by the score on the BSI scale and to determine a statistical significance of the reduction in suicidality. A 2-tailed paired t-test was used for within group comparisons.

As shown in FIGS. 2A and 2B, buprenorphine was considerably more effective than a placebo at reducing mean total BSI scores as compared to baseline scores during the study period. Buprenorphine treatment reduced average BSI scores from 20.2±4.2 to 8.2±7.7 (average improvement of 12.0±8.2), a statistically significant improvement ($t[24]=7.33$, $p<0.01$), whereas placebo treatment reduced average BSI scores from 19.5±5.8 to 14.3±10.7 (average improvement of 5.2±11.7), which was not a statistically significant change ($t[13]=1.67$, p=ns). The average improvement obtained from buprenorphine treatment (12.0±8.2) was greater than that obtained from placebo treatment (5.2±11.7) in a statistically significant manner, with LOCF (last observation carried forward) analysis ($t[37]=-2.1$, $p<0.05$).

As further shown in FIGS. 2A and 2B, both buprenorphine and placebo significantly reduced BSI scores during the first week, although the placebo effect eroded gradually thereafter. During the first week, buprenorphine treatment reduced average BSI scores from 20.2±4.2 to 12.4±7.7 ($t[23]=6.2$, $p<0.01$), whereas placebo treatment reduced average BSI scores from 19.5±5.8 to 11.8±10.3 ($t[11]=3.25$, $p<0.01$).

These results indicate that during the first week, the effect of buprenorphine on BSI scores is not medication-specific, and are consistent with the results presented in Example 1. These results further indicate that the placebo effect begins to disappear after the first week, and the effect of buprenorphine after the first week is medication-specific.

In order to help differentiate between buprenorphine-specific effects and placebo effects, BSI scores were evaluated for the subset of subjects who received a final dose (of buprenorphine or placebo) of 0.4 mg or more.

As shown in FIG. 3, the effect of buprenorphine vs. that of placebo is especially pronounced in subjects who received a final dose of 0.4 mg or more. In such cases, buprenorphine treatment reduced average BSI scores from 21.0±4.8 to 11.8±8.8 (t[11]=4.44, p<0.01) in week 1, and from 11.8±8.8 to 5.1±7.3 from week 1 to week 4 (t[n]=2.59, p<0.05). In comparison, placebo treatment reduced average BSI scores from 18.4±5.9 to 12.5±11.2 (t[7]=2.53, p<0.05) in week 1, but BSI scores then increased from 12.5±11.2 to 18.2±10.0 from week 1 to week 4 (t[7]=−3.43, p<0.05). The effect of buprenorphine treatment was statistically different from the effect of placebo, with LOCF analysis (t[20]=−3.1, p<0.01) or without LOCF analysis (t[16]=−3.2, p<0.01).

The effect of buprenorphine dose on common side effects of opioid medications (nausea, vomiting, headache, constipation, dizziness, sweating) was evaluated by measuring the emergence of side effects during a week of treatment as a function of medication dose during that week.

As shown in FIG. 4, administration of 0.2 mg/day or more of buprenorphine resulted in a an increased level of side effects as compared to placebo treatment, whereas administration of 0.1 mg/day of buprenorphine did not result in increased side effects. The results obtained for 0.1 mg/day buprenorphine were statistically different than the results obtained for 0.2 mg/day ($\chi^2(1, N=102)=2.722$, p<0.05), for 0.4 mg/day ($\chi^2(1, N=84)=3.357$, p<0.05), and for >0.4 mg/day ($\chi^2(1, N=62)=3.187$, p<0.05).

The effect of buprenorphine dose on severe side effects was also evaluated by measuring the percentage of subjects who discontinued the study due to side effects, as a function of the starting dose.

Among subjects receiving a starting dose of more than 0.1 mg/day buprenorphine, 26% (10/38) eventually discontinued the study due to side effects, whereas among subjects receiving a starting dose of 0.1 mg/day buprenorphine, only 13% (3/23) eventually discontinued the study due to side effects.

These results indicate that administration of buprenorphine at a dose of approximately 0.1 mg/day can reduce side effect-related dropout rates by 50%, thereby enhancing compliance with buprenorphine treatment.

In view of the above-described effectiveness of a starting dose of 0.1 mg/day buprenorphine at reducing a side effect-related dropout rate, the effect of such a starting dose on final outcome (final BSI score vs. baseline BSI score) was evaluated.

In subjects receiving a starting dose of 0.1 mg/day buprenorphine, the final BSI score was reduced relative to baseline by 11.8±7.8 (n=11), whereas in subjects receiving a starting dose of >0.1 mg/day buprenorphine, the final BSI score was reduced relative to baseline by 12.2±8.8 (n=14). This difference was not statistically significant (t[23]=0.11).

These results indicate that a starting dose of approximately 0.1 mg/day buprenorphine can reduce side effect levels and side effect-related dropout rates, without compromising final outcome relative to higher starting doses. This advantage is of considerable importance for treating a highly unstable and suicide-prone patient population, in whom treatment adherence is a top priority.

The efficacy of various doses of buprenorphine at reducing suicidality was evaluated by measuring improvement in BSI scores relative to baseline as a function of the dose of medication (buprenorphine or placebo). For example, if a subject received 0.1 mg/day during weeks 1 and 2, and 0.2 mg/day during weeks 3 and 4, the improvement in BSI scores was represented by 2 data points, one for the average of weeks 1 and 2 (relative to baseline) and one for the average of weeks 3 and 4 (relative to baseline.

As shown in FIG. 5, doses of 0.1, 0.2, 0.4 and >0.4 mg/day buprenorphine each resulted in a reduction of BSI scores relative to baseline. The improvement in BSI scores associated with buprenorphine was statistically significant relative to placebo at doses of 0.1 mg/day ($\chi^2(1, N=14)=$−4.43, p<0.05), 0.4 mg/day ($\chi^2(1, N=20)=6.87$, p<0.01), and >4 mg/day ($\chi^2(1, N=13)=4.01$, p<0.05), but not at 0.2 mg/day ($\chi^2(1, N=22)=$−0.40, p=ns).

As further shown therein, the effect of buprenorphine was moderately dose-dependent, with 0.4 and >0.4 mg/day resulting in the largest changes. However, administration of >0.4 mg/day showed no advantage over administration of 0.4 mg/day. In contrast, the results for placebo treatment were not dose-dependent.

These results indicate that administration of 0.1 mg/day buprenorphine has significant efficacy at reducing suicidality, consistent with the above-described finding that a starting dose of 0.1 mg/day buprenorphine does not compromise final outcome.

These results further indicate that doses in a range of approximately 0.1 to approximately 0.4 mg/day are particularly effective at reducing suicidality while minimizing side effects by avoiding unnecessarily high doses.

In addition, the effect of various doses was further evaluated by examining the relationship of the final administered dose (i.e., at week 4 of the study) of buprenorphine or placebo to the change in BSI score (i.e., at week 4). In addition, the relationship of the administered doses (i.e., regardless of time) of buprenorphine or placebo to the change in BSI scores from baseline were examined. The aforementioned evaluations used Spearman correlations and LOCF analysis.

As shown in FIGS. 6A and 6B, the change in BSI scores was negatively correlated to the final buprenorphine doses (n=24, r=−0.353, p=0.090, but positively correlated with the final placebo doses (n=12, r=0.585, p=0.046).

The correlation between high placebo dose and high suicidality is likely a result of the study design, which prompted the treating physicians to increase doses (including placebo doses) in subjects exhibiting an insufficient decrease in suicidality. That the final buprenorphine dose was correlated with reduction in BSI scores, despite the study design which biases the results in the opposite direction (e.g., as described hereinabove for the placebo) further confirms that the effect of buprenorphine is dose-dependent.

In addition, examination of all doses given to subjects, regardless of time, showed a significant correlation of buprenorphine dose to changes in BSI scores (r=−0.251, p=0.0017, whereas there was no significant correlation of placebo dose to change in BSI scores (r=0.005, p=ns). These results further confirm that the effect of buprenorphine is dose-dependent.

The above results further indicate that the reduction of suicidality by buprenorphine administration is time-dependent in addition to being dose-dependent. For example, the decline in BSI scores after 4 weeks of treatment was greater than the decline in BSI scores after 2 weeks in the pilot study described in Example 1, despite the fact that the pilot study used considerably higher buprenorphine doses (~0.8-1.6 mg/day in the last week of the pilot study vs. ~0.4-0.6 mg/day in the last week of the later study). In addition, both studies show a significant placebo effect which disappears over time. Thus, the results indicate that buprenorphine treatment for 4 weeks is more effective than buprenorphine treatment for 2 weeks.

The obtained data was further analyzed in order to determine whether the reduction in suicidality by buprenorphine is a result of an antidepressant effect of buprenorphine in suicidally depressed patients.

As shown in FIG. 7 and in Table 2, buprenorphine reduced suicidality in patients without major depressive disorder (mainly patients diagnosed with adjustment disorders) at least as much as in patients with major depressive disorder. This suggests that the effect of buprenorphine was not the result of a reduction in depression.

As further shown in Table 2, there was no association between reduction of suicidality and personality disorder, acute axis 4 stressor, or chronic treatment with antidepressants, as determined by an independent 2-tailed t-test.

TABLE 2

Average decrease in BSI score in the presence or absence of various risk factors for suicidality

| | Decrease in BSI score | | |
|---|---|---|---|
| Factor | With | Without | Statistical Significance |
| Major Depressive Disorder | 10.0 (n = 15) | 14.4 (n = 10) | none |
| Personality Disorder | 12.0 (n = 14) | 12.0 (n = 11) | none |
| Acute Axis 4 Stressor | 13.6 (n = 11) | 10.8 (n = 14) | none |
| Chronic Treatment with Antidepressants | 12.7 (n = 17) | 10.5 (n = 8) | none |

In order to further ascertain whether the reduction in suicidality is a result of an antidepressant effect, the relationships between suicidality (as assessed by BSI), depressive symptoms (as assessed by BDI), and mental pain (as assessed by Holden's Psychache Scale were determined.

As shown in FIG. 8, prior to treatment, mental pain was strongly correlated to depressive symptoms (Spearman r=0.7395), whereas the correlations between suicidality and mental pain (Spearman r=0.4329), and suicidality and depressive symptoms (Spearman r=0.4245), were considerably lower. These results suggest that suicidality is a distinct symptom from depressive symptoms and mental pain.

As shown in FIG. 9, the effect of placebo treatment on suicidality was strongly correlated to its effect on depressive symptoms (Pearson r=0.826, p<0.01), whereas the effect of buprenorphine treatment on suicidality was considerably less correlated to the effect of buprenorphine on depressive symptoms (Pearson r=0.473, 0.01<p<0.05). In the buprenorphine-treated group, the slope of change in BSI scores as a function of change in BDI scores was considerably lower than the slope in the placebo group (Sig=0.07).

Because buprenorphine has been reported to have an antidepressant effect, albeit in doses generally higher than those used herein, the magnitude of buprenorphine on BDI scores in the patient population was examined, and compared to the effects of placebo.

As shown in FIG. 10, administration of buprenorphine at dosages described herein had relatively little effect on BDI scores. There was no statistically-significant difference in its effects on total BDI scores when compared to placebo during all 4 weeks of the study, including when the results in week 4 were compared by LOCF analysis. In addition, the relative magnitude of the average reduction in BDI scores in the buprenorphine group (from ~40 to ~25, about 38%) was much smaller than the relative magnitude of the average reduction in BSI scores in the buprenorphine group (from ~20 to ~8, about 80%, see FIG. 2A).

Similarly, when the effect of buprenorphine on changes in BDI scores was assessed compared to baseline, no significant differences from placebo were observed during all 4 weeks of the study. However, when the results in week 4 were compared by LOCF, there was a significant change from placebo (t[37]=−2.06, p<0.05). This finding is consistent with the findings in Example 1 in which higher doses of buprenorphine were used, and the relative magnitude of the average reduction in BDI scores was about 50% in 2 weeks (from ~32 to ~16, see Table 1).

Taken together, these results indicate that at relatively low doses such as described herein, the effect of buprenorphine on suicidality is distinct from its effect on depressive symptoms.

Example 3

Phase III Clinical Study of the Effect of Low-Dose Buprenorphine Treatment on Acute Suicidality In order to investigate the efficacy of starting doses of less than 0.1 mg/day of buprenorphine, a phase III placebo-controlled double-blind study is performed as described in Example 2, except with administration of lower doses. Starting doses (e.g., for the first two weeks) are 0.05 mg/day (buprenorphine or placebo), followed by 0.1 mg/day (e.g., for the next two weeks). The dose is then optionally raised to above 0.1 mg/day, as described in Example 2.

Example 4

Phase III Clinical Study of the Effect of Buprenorphine Treatment in Divided Doses on Acute Suicidality In order to investigate the efficacy of divided doses of buprenorphine (0.05 and 0.1 mg twice a day), a phase III placebo-controlled double-blind study is performed as described in Example 2, except with twice a day administration. Starting doses (e.g., for the first two weeks) are either 0.05 mg (buprenorphine or placebo) twice a day, followed by 0.1 mg twice a day (e.g., for the next two weeks), or 0.1 mg (buprenorphine or placebo) twice a day (e.g., for the first two weeks), followed by 0.2 mg twice a day (e.g., for the next two weeks). The dose is then optionally raised to above 0.2 or 0.4 mg/day, respectively, as described in Example 2.

Example 5

Phase III Clinical Study of the Effects of Buprenorphine Treatment on Brain Activity and on the Perception of Physical Pain in Patients with Acute Suicidality In order to investigate the mechanisms of action of buprenorphine (0.1 to 0.4 mg/day) in acute suicidality, an open-label study is performed as described in Example 2, except without a placebo group, and with additional laboratory studies as described below.

Patients' regional cerebral metabolic activity is assessed with fMRI at baseline and again following 4 weeks of treatment. Patients' nociception is similarly assessed with contact heat stimulation (for pain threshold and pain sensitivity) at baseline and again following 4 weeks of treatment.

It is hypothesized that following treatment, the magnitude of improvement in suicidality will be correlated with a decrease in regional cerebral metabolism in the anterior cingulate gyrus (ACC) and anterior insula (AI) bilaterally, as well as in other cerebral loci. It is further hypothesized that lower pain thresholds and higher pain ratings at baseline will also be correlated with the magnitude of improvement in suicidality. Starting doses (e.g., for the first week) are 0.1 mg/day, or 0.1 mg (buprenorphine or placebo) twice a day, followed by 0.2 mg/day, or 0.2 mg twice a day (e.g., for the next two weeks). The dose is then optionally raised to above 0.2 or 0.4 mg/day, respectively, as described in Example 2.

Example 6

Phase III Clinical Study of the Effect of Buprenorphine Treatment on Chronic Suicidality In order to investigate the efficacy of buprenorphine (0.05 to 0.4 mg/day), on chronic suicidality, a phase III placebo-controlled double-blind study is performed as described in Example 2, with the following changes:

First, subjects are those suffering from chronic suicidality (i.e., have been suicidal most of the time, for more than 6 months, during the time period immediately before entering the study); second, the study medication (buprenorphine or placebo) is administered for 12 weeks; and third, in addition to their weekly assessments while receiving the study medication and one week thereafter, subjects are seen for a follow-up assessment 4 weeks after completing the medication phase of the study.

Starting doses (e.g., for the first two weeks) are either 0.05 mg (buprenorphine or placebo) once or twice a day, followed by 0.1 mg once or twice a day (e.g., for the next two weeks), or 0.1 mg (buprenorphine or placebo) twice a day, followed by 0.2 mg twice a day (e.g., for the next two weeks). The dose is then optionally raised to above 0.2 or 0.4 mg/day, respectively, as described in Example 2.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating acute suicidality in a subject in need thereof, the method being effected by administering to a subject determined as having acute suicidality a therapeutically effective amount of buprenorphine, or a pharmaceutically acceptable salt thereof, thereby treating said acute suicidality in a subject in need thereof, wherein said subject is not afflicted by a depressive disorder.

2. The method of claim 1, wherein said subject is not afflicted by a borderline personality disorder.

3. The method of claim 1, comprising:
(a) determining a presence of acute suicidality in a subject; and
(b) administering to a subject determined as having acute suicidality a first therapeutically effective amount of buprenorphine, or a pharmaceutically acceptable salt thereof, during a first time period, said first therapeutically effective amount being less than 0.2 mg per day, and said first time period ranging from 3 days to 3 weeks; and
(c) following said first time period, determining a responsiveness of the subject to said first therapeutically effective amount, to thereby determine if the subject is not fully responsive to said first therapeutically effective amount; and
(d) if the subject is determined as not fully responsive to said first therapeutically effective amount, administering to the subject, during a second time period, a second therapeutically effective amount of buprenorphine, said second therapeutically effective amount being higher than said first therapeutically effective amount.

4. The method of claim 3, further comprising, following said administering said second therapeutically effective amount of buprenorphine during said second time period:
(e) determining a responsiveness of the subject to said second therapeutically effective amount, to thereby determine if the subject is not fully responsive to said second therapeutically effective amount; and
(f) if the subject is determined as not fully responsive to said second therapeutically effective amount, administering to the subject, during a third time period, a third therapeutically effective amount of buprenorphine, said third therapeutically effective amount being higher than said second therapeutically effective amount.

5. The method of claim 1, comprising:
determining a presence of acute suicidality in a subject; and
administering to a subject determined as having acute suicidality a first therapeutically effective amount of buprenorphine, or a pharmaceutically acceptable salt thereof, during a first time period, said first therapeutically effective amount being less than 0.2 mg per day.

6. The method of claim 1, wherein administering buprenorphine is effected for a total time period that ranges from one week to four weeks.

7. The method of claim 1, wherein said subject is afflicted by a disorder selected from the group consisting of a personality disorder, a psychosis, a substance abuse disorder, an anxiety disorder, an eating disorder, an attention deficit disorder, a tic disorder, a gender dysphoria, a dissociative disorder, a somatoform disorder, an impulse control disorder and an adjustment disorder.

8. The method of claim 1, wherein said subject is afflicted by a disorder selected from the group consisting of anorexia nervosa, a posttraumatic stress disorder, an adjustment disorder, schizophrenia, a borderline personality disorder, a narcissistic personality disorder, an antisocial personality disorder, an intermittent explosive disorder, an attention deficit disorder, a tic disorder, a panic disorder, a body dysmorphic disorder, a dissociative identity disorder, a social anxiety disorder, a substance abuse disorder, a bipolar disorder, and a gender dysphoria.

9. The method of claim 1, wherein said determining comprises measuring suicidality on a scale selected from the group consisting of a Beck Suicidal Ideation (BSI) scale, a Suicide Probability Scale (SPS), a Columbia Suicide Severity Rating Scale (C-SSRS), and an Overt Aggression Scale Modified (OAS-M).

10. The method of claim 1, wherein said administering is effected by a route selected from the group consisting of sublingual administration and transdermal administration.

11. The method of claim 1, wherein said therapeutically effective amount is in a range of from 0.02 to 0.15 mg per day.

12. The method of claim 3, wherein said second therapeutically effective amount is 0.5 mg per day or less.

* * * * *